US011377466B2

(12) United States Patent
Chau et al.

(10) Patent No.: US 11,377,466 B2
(45) Date of Patent: Jul. 5, 2022

(54) ANALOGS OF THE NATURAL PRODUCT ICARIIN

(71) Applicant: Whitehead Institute for Biomedical Research, Cambridge, MA (US)

(72) Inventors: Yasmin Chau, Cambridge, MA (US); Fu-Shuang Li, Quincy, MA (US); Jing-Ke Weng, Belmont, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 17/265,081

(22) PCT Filed: Aug. 7, 2019

(86) PCT No.: PCT/US2019/045435
§ 371 (c)(1),
(2) Date: Feb. 1, 2021

(87) PCT Pub. No.: WO2020/033498
PCT Pub. Date: Feb. 13, 2020

(65) Prior Publication Data
US 2021/0309684 A1    Oct. 7, 2021

Related U.S. Application Data

(60) Provisional application No. 62/717,318, filed on Aug. 10, 2018.

(51) Int. Cl.
*C07H 17/07* (2006.01)
*C07H 15/26* (2006.01)
*C07D 311/28* (2006.01)

(52) U.S. Cl.
CPC .......... *C07H 17/07* (2013.01); *C07D 311/28* (2013.01); *C07H 15/26* (2013.01)

(58) Field of Classification Search
None
See application file for complete search history.

(56) References Cited

U.S. PATENT DOCUMENTS 9,572,848 B1   2/2017 Vascoe et al.
2010/0016352 A1  1/2010 Li et al.

FOREIGN PATENT DOCUMENTS

CN           1884275 A    12/2006
WO    WO 2008014722 A1   2/2008
WO    WO-2018014722 A1 * 1/2018 .......... A61B 5/6807

OTHER PUBLICATIONS

Wang et al., European Journal of Medicinal Chemistry, 100, 2015, pp. 139-150. (Year: 2015).*

Chen, G., et al., "An Insight into the Pharmacophores of Phosphodiesterase-5 Inhibitors Torn Synthetic and Crystal Structural Studies", *Biochem. Pharmacol.* 2008, 75 (9), 1717-1728.
Dell'Agli, M., et al., "Potent Inhibition of Human Phosphodiesterase-5 by Icariin Derivatives" *J. Nat. Prod.* 2008, 71 (9), 1513-1517.
Emsley, P., et al., "Coot: Model-Building Tools for Molecular Graphics", *Acta Crystallogr. D Bio ,. Crystallogr.* 2004, 60 (Pt 12 Pt 1), 2126-2132.
Emsley, P., et al., "Features and Development of Coot. *Acta Crystallogr. D Biol. Crystallogr*", 2010, 66 (Pt 4), 486-501.
Friebe, A., et al., "A. Meeting Report of the 8th International Conference on cGMP cGMP: Generators, Effectors, and Therapeutic Implications" at Bamberg, Germany, from Jun. 23 to 25, 2017. *Naunyn. Schmiedebergs. Arch. Pharmacol.* 2017, 390 (12), 1177-1188.
Hanwell, M. D., et al., "An Advanced Semantic Chemical Editor, Visualization, and Analysis Platform" *J. Cheminform.* 2012, 4 (1), 17.
Huai, Q., et al., "Crystal Structures of Phosphodiesterases 4 and 5 in Complex with Inhibitor 3-Isobutyl-1-Methylxanthine Suggest a Conformation Determinant of Inhibitor selectivity", *J. Biol. Chem.* 2004, 279 (13), 13095-13101.
International Preliminary Report on Patentability for International Application No. 3CT/US2019/45435 "Analogs of the Natural Product Icariin", dated Feb. 16, 2021.
Ke, H., et al., "Crystal Structures of Phosphodiesterases and Implications on Substrate specificity and Inhibitor Selectivity", *Curr. Top. Med. Chem.* 2007, 7 (4), 391-403.
Kim, D. H., et al., "Potential of Icariin Metabolites from Epimedium Koreanum Nakai as Antidiabetic Therapeutic Agents", *Molecules* 2017, 22 (6).
Li, F.-S., et al., Demystifying Traditional Herbal Medicine with Modern Approach. *Nature Plants* 2017, 3 (8), 17109.
Liu, D. F., et al., "Synthesis and Antimultidrug Resistance Evaluation of Icariin and Its Derivatives", *Bioorg. Med. Chem. Lett.* 2009, 19 (15), 4237-4240.
Lyskov, S., et al., "Serverification of Molecular Modeling Applications: The Rosetta Online Server That Includes Everyone (ROSIE)", *PLoS One* 2013, 8 (5), e63906.
Ma, H., et al., "The Genus Epimedium: An Ethnopharmacological and Phytochemical Review" *J. Ethnopharmacol.* 2011, 134 (3), 519-541.
Mehrotra, N., et al., "The Role of Pharmacokinetics and Pharmacodynamics in Phosphodiesterase-5 Inhibitor Therapy", *Int. J. Impot. Res.* 2007, 19 (3), 253-264.

(Continued)

*Primary Examiner* — Traviss C McIntosh, III
(74) *Attorney, Agent, or Firm* — Hamilton, Brook, Smith & Reynolds, P.C.

(57) ABSTRACT

Provided herein are analogs of the natural product icariin represented by Structural Formula (I) or a pharmaceutically acceptable salt thereof. The analogs can be used to modulate (e.g., inhibit, such as by competitive inhibition) PDE5 and thereby treat a wide range of PDE5-mediated diseases, including cardiovascular, gastrointestinal, pulmonary, musculoskeletal, neurological and reproductive diseases. Also provided herein are compositions and methods including compounds of Structural Formula (I).

24 Claims, 12 Drawing Sheets
(12 of 12 Drawing Sheet(s) Filed in Color)

(56) References Cited

OTHER PUBLICATIONS

Ming, L. G., et al., "Functions and Action Mechanisms of Flavonoids Genistein and Icariin in Regulating Bone Remodeling", *J. Cell. Physiol.* 2013, 228 (3), 513-521.

Mostafa, T. "Non-Sexual Implications of Phosphodiesterase Type 5 Inhibitors. *Sexual Medicine Reviews*" 2017, 5 (2), 170-199.

Ning, H., et al., "Effects of Icariin on Phosphodiesterase-5 Activity in Vitro and Cyclic Guanosine Monophosphate Level in Cavernous Smooth Muscle Cells", Urology 2006, 68 (6), 1350-1354.

Notification of Transmittal of The International Search Report and The Written Opinion of the International Searching Authority, or the Declaration for International Application No. PCT/US2019/045435 "Analogs of the Natural Product Icariin", dated Oct. 15, 2019.

Schluesener, J. K., et al., "Plant Polyphenols in the Treatment of Age-Associated Diseases: Revealing the Pleiotropic Effects of Icariin by Network Analysis", *Mol. Nutr. Food Res.* 2014, 58 (1), 49-60.

Shang, N.-N et al., "Discovery of 3-(4-Hydroxybenzyl)-1-(thiophen-2-Yl) Chromeno [2, 3-C] Pyrrol-9 (2H)-One as a Phosphodiesterase-5 Inhibitor and Its Complex Crystal Structure", *Biochem. Pharmacol.* 2014, 89 (1), 86-98.

Wang, H., et al., "Conformational Variations of Both Phosphodiesterase-5 and Inhibitors Provide the Structural Basis for the Physiological Effects of Vardenafil and Sildenafil", *Mol. Pharmacol.* 2008, 73, 104-110.

Wang, H., et al., "Multiple Conformations of Phosphodiesterase-5: Implications for Enzyme Function and Drug Development", *J. Biol. Chem.* 2006, 281 (30), 21469-21479.

Xin, Z. C., et al., "Effects of Icariin on cGMP-Specific PDE5 and cAMP-Specific PDE4 Activities", *Asian J. Androl.* 2003, 5 (1), 15-18.

Xin, Z., et al., "Icariin on Relaxation Effect of Corpus Cavemosum Smooth Muscle", *Chin. Sci. Bull.* 2001, 46 (14), 1186-1190.

Zhang, J., et al., "Effect of Icarisid II on diabetic rats with erectile dysfunction and its potential mechanism via assessment of AGEs, autophagy, mTOR and the NO-cGMP pathway", Asian Journal of Andrology, vol. 15, 2013, pp. 143-148.

Zhang, K. Y. J., et al., "A Glutamine Switch Mechanism for Nucleotide Selectivity by Phosphodiesterases", *Mol. Cell* 2004, 15 (2), 279-286.

* cited by examiner

ANALOGS OF THE NATURAL PRODUCT ICARIIN

RELATED APPLICATIONS

This application is the U.S. National Stage of International Application No. PCT/US2019/045435, filed on Aug. 7, 2019, which designates the U.S., published in English, and claims the benefit of U.S. Provisional Application No. 62/717,318, filed on Aug. 10, 2018. The entire teachings of the above applications are incorporated herein by reference.

BACKGROUND

Cyclic nucleotide phosphodiesterases (PDEs) are key regulators of intracellular levels of the highly conserved second messenger molecules cyclic guanosine monophosphate (cGMP) and cyclic adenosine monophosphate (cAMP) in eukaryotes. cGMP and cAMP are synthesized by cyclases in response to upstream signals such as hormones or neurotransmitters, and modulate a variety of downstream processes, such as cell contractility, cell growth and proliferation, inflammation, sensory transduction, and neuronal plasticity. PDEs turn off this signaling pathway by hydrolyzing cyclic nucleotides to produce the corresponding 5'-monophosphates GMP and AMP. Each of the twenty-one PDEs encoded by the human genome possesses characteristic substrate specificity and tissue expression pattern, playing distinct roles in normal physiology and diseases. As a result, various PDE inhibitors have long been developed as therapeutics with diverse disease indications.

Phosphodiesterase 5 (PDE5) is a cGMP-specific PDE expressed predominantly in smooth muscle cells, platelets, and cardiomyocytes. PDE5 inhibitors have been commercially successful PDE-targeting therapeutics. In particular, sildenafil (Viagra, Revatio), vardenafil (Levitra), and tadalafil (Cialis, Adcirca) are FDA-approved drugs that treat erectile dysfunction and pulmonary hypertension. These drugs function as competitive inhibitors of PDE5 with $IC_{50}$s in the low nanomolar range (sildenafil, 1-9 nM; vardenafil, 0.1-0.8 nM; tadalafil, 1-7 nM). Furthermore, recent studies suggest that PDE5 is a viable therapeutic target for the treatment of a wide range of illnesses, including cardiovascular, gastrointestinal, pulmonary, musculoskeletal, neurological, and reproductive diseases.

The horny goat weed, referring to several species belonging to the Epimedium family, has been used for thousands of years as a traditional herbal medicine in China to treat sexual dysfunction. Previous work identified the prenylated flavonoid icariin and its naturally occurring analogs as the principle bioactive components in Epimedium plants. Icariin is a competitive inhibitor of human PDE5 with an $IC_{50}$ in the low to mid micromolar range (1-6 μM). Like several synthetic PDE5 inhibitors, icariin can increase cGMP levels in cavernous smooth muscle cells isolated from icariin-treated mice. However, the full potential of the structure space based on the icariin backbone has not been fully explored.

Accordingly, there is a need for additional analogs of the natural product icariin that can be used to target PDE5 and thereby treat a wide range of diseases, disorders and conditions.

SUMMARY

Provided herein are analogs of the natural product icariin. The analogs can be used to modulate (e.g., inhibit, such as by competitive inhibition) PDE5 and thereby treat a wide range of PDE5-mediated diseases, disorders and conditions, including cardiovascular, gastrointestinal, pulmonary, musculoskeletal, neurological and reproductive diseases, disorders and conditions. Also provided herein are compositions and methods including analogs of the natural product icariin.

One embodiment is a compound of Structural Formula I:

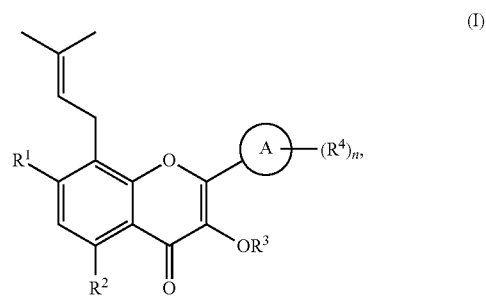

or a pharmaceutically acceptable salt thereof, wherein values for the variables (e.g., $R^1$, $R^2$, $R^3$, $R^4$, Ring A and n) are as described herein. Also provided is a composition comprising a compound of Structural Formula I, or a pharmaceutically acceptable salt thereof, and a pharmaceutically acceptable carrier or excipient.

Another embodiment is a method of treating a PDE5-mediated disease in a subject in need thereof, comprising administering to the subject a compound of Structural Formula I, or a pharmaceutically acceptable salt thereof. Also provided is a compound for use in the treatment of a PDE5-mediated disease, wherein the compound is represented by Structural Formula I, or a pharmaceutically acceptable salt thereof. Also provided is use of a compound of Structural Formula I, or a pharmaceutically acceptable salt thereof, for the manufacture of a medicament for the treatment of a PDE5-mediated disease.

Yet another embodiment is a method of treating a disease, disorder or condition described herein in a subject in need thereof, comprising administering to the subject an effective amount of a compound of Structural Formula I, or a pharmaceutically acceptable salt thereof. Also provided is a compound for use in the treatment of a disease, disorder or condition described herein, wherein the compound is represented by Structural Formula I, or a pharmaceutically acceptable salt thereof. Also provided is use of a compound of Structural Formula I, or a pharmaceutically acceptable salt thereof, for the manufacture of a medicament for the treatment of a disease, disorder or condition described herein.

Compounds 3 and 7 described herein can be used to inhibit PDE5 with an $IC_{50}$ and $K_i$ similar to the $IC_{50}$ and $K_i$ of other synthetic, FDA-approved PDE5 inhibitors, including sildenafil.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1A:
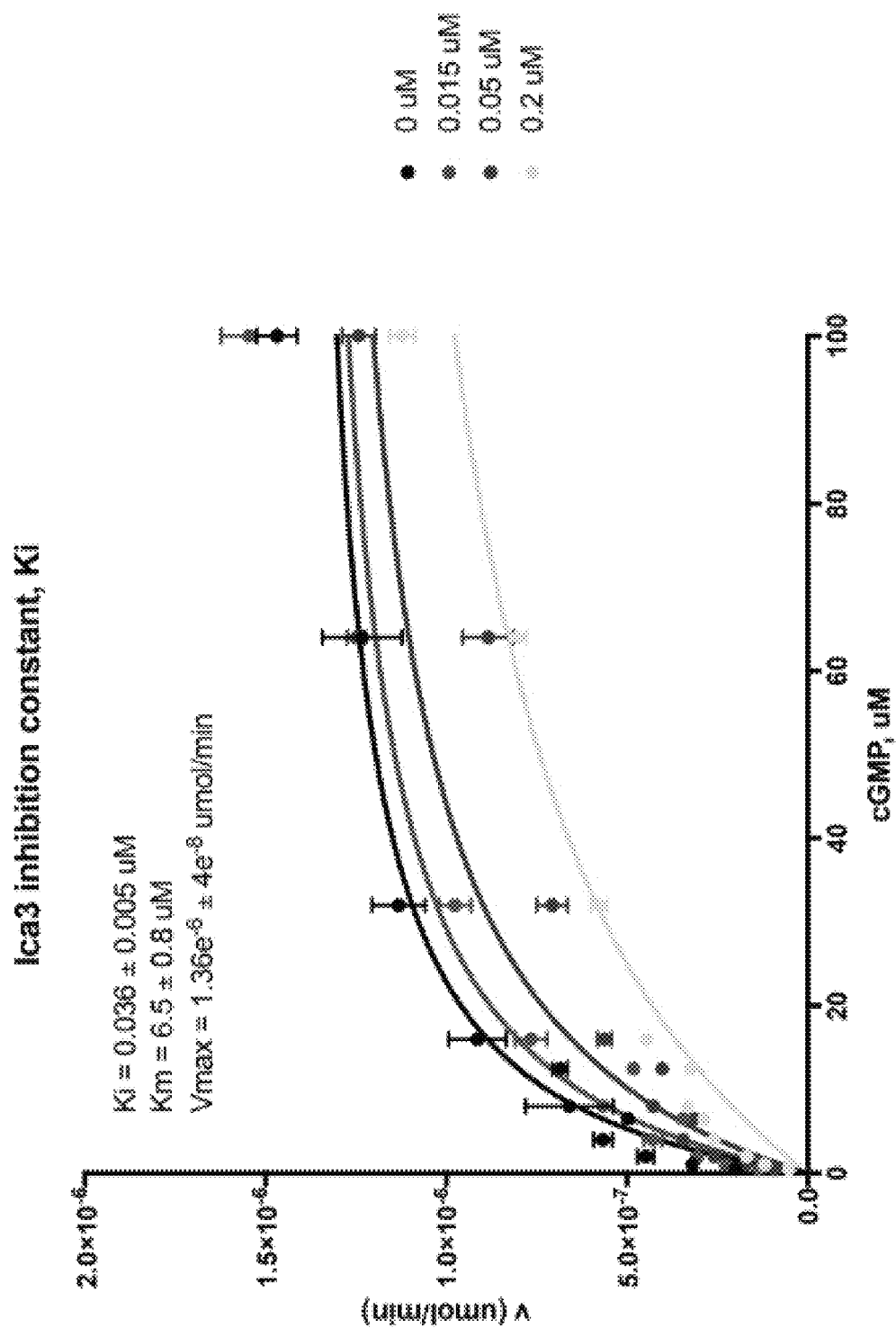
FIG. 1A is an enzyme kinetic curve obtained with Ica3.

A description of example embodiments follows.

Definitions

Compounds described herein include those described generally, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are incorporated herein by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its chemical structure names and rules on naming chemical structures. Optionally, a name of a compound may be generated using a chemical naming program (e.g., CHEMDRAW®, version 17.0.0.206, PerkinElmer Informatics, Inc.).

Compounds of the present invention may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers or enantiomers, with all possibR[1] isomers and mixtures thereof, including optical isomers, being included in the present invention.

"Alkyl" refers to an optionally substituted, saturated, aliphatic, branched or straight-chain, monovalent, hydrocarbon radical having the specified number of carbon atoms. Thus, "$(C_1-C_5)$alkyl" means a radical having from 1-5 carbon atoms in a linear or branched arrangement. Alkyl includes, but is not limited to, methyl, ethyl, propyl, isopropyl, butyl, isobutyl, sec-butyl, pentyl, etc.

"Alkenyl" refers to an optionally substituted, aliphatic, branched or straight-chain, monovalent, hydrocarbon radical having at least one carbon-carbon double bond and the specified number of carbon atoms. Thus, "$(C_1-C_5)$alkenyl" means a radical having at least one carbon-carbon double bond and from 1-5 carbon atoms in a linear or branched arrangement. Alkenyl includes, but is not limited to, allyl, vinyl and isoprenyl.

"Alkynyl" refers to an optionally substituted, aliphatic, branched or straight-chain, monovalent, hydrocarbon radical having at least one carbon-carbon triple bond and the specified number of carbon atoms. Thus, "$(C_1-C_5)$alkynyl" means a radical having at least one carbon-carbon triple bond and from 1-5 carbon atoms in a linear or branched arrangement. Alkynyl includes, but is not limited to, propargyl.

"Acyl" means —C(O)alkyl, wherein alkyl is as described herein. In one embodiment, acyl is —C(O)$(C_1-C_{10})$alkyl.

"Alkanoyl" means —C(O)O-alkyl, wherein alkyl is as described herein. In one embodiment, alkanoyl is —C(O)O$(C_1-C_{10})$alkyl.

"Amido" means —C(O)RR', wherein R and R' are independently selected from hydrogen or $(C_1-C_{10})$alkyl, wherein the alkyl groups may be the same or different and alkyl is as described herein. In one aspect, R and R' are independently selected from hydrogen or $(C_1-C_5)$alkyl. Examples of amido include, but are not limited to, —C(O)$NH_2$.

"Amino" means —$NH_2$.

"Alkylamino" means (alkyl)(H)—N—, wherein alkyl is as described herein. In one aspect, an alkylamino is a $(C_1-C_5)$alkylamino. Particular alkylamino groups include, but are not limited to, methylamino, ethylamino, propylamino and isopropylamino.

"Carbocyclyl" refers to an optionally substituted, saturated or unsaturated, aliphatic or aromatic, monocyclic or polycyclic (e.g., bicyclic, tricyclic), monovalent ring system having the specified number of ring atoms. Thus, "$(C_3-C_{15})$carbocyclyl" means a ring system having from 3 to 15 carbon atoms. A carbocyclyl can be monocyclic, fused bicyclic, bridged bicyclic or polycyclic. A carbocyclyl can be saturated (i.e., a cycloalkyl). Alternatively, a carbocyclyl can be unsaturated (i.e., contain at least one degree of unsaturation, as in at least one double bond or triple bond) or aromatic (i.e., an aryl). Examples of monocyclic carbocyclyls include, but are not limited to, cycloalkyl, cycloalkenyl, cycloalkynyl and phenyl.

"Aryl" refers to an optionally substituted, monocyclic or polycyclic (e.g., bicyclic, tricyclic), carbocyclic, aromatic ring system having the specified number of ring atoms. Thus, "$(C_6-C_{15})$aryl" means a ring system having from 6-15 carbon atoms. Aryl includes, but is not limited to, phenyl, napthyl, indenyl, and anthracenyl. In a preferred embodiment, aryl is phenyl. Typically, aryl has 6 to 13, 6 to 10, 6 to 9, or 6 carbon atoms.

"Cycloalkyl" refers to an optionally substituted, saturated, aliphatic, monovalent, monocyclic or polycyclic, hydrocarbon ring radical having the specified number of ring atoms.

Thus, "($C_3$-$C_8$)cycloalkyl" means a ring radical having from 3-8 ring carbons. Typically, cycloalkyl is monocyclic. In one embodiment, cycloalkyl is ($C_3$-$C_8$)cycloalkyl. Cycloalkyl includes, but is not limited to, cyclopropyl, cyclobutyl, cyclopentyl, cyclohexyl, cycloheptyl, cyclooctyl and adamantyl.

"Ether" refers to an optionally substituted, saturated, aliphatic, branched or straight-chain, monovalent, hydrocarbon radical having the specified number of carbon atoms, wherein at least one (e.g., 1, 2 or 3) carbon atoms has been replaced with an oxygen atom. Thus, "($C_1$-$C_{10}$)ether" means a radical having from 1 to 10 carbon atoms in a linear or branched arrangement, wherein at least one of the carbon atoms has been replaced with an oxygen atom.

"Formyl" means —C(O)H.

"Heteroaryl" refers to an optionally substituted, monocyclic or polycyclic (e.g., bicyclic, tricyclic), aromatic, hydrocarbon ring system having the specified number of ring atoms, wherein at least one carbon atom in the ring system has been replaced with a heteroatom selected from N, S and O. Thus, "($C_5$-$C_{15}$)heteroaryl" means a heterocyclic aromatic ring system having from 5-15 ring atoms consisting of carbon, nitrogen, sulfur and oxygen. A heteroaryl can contain 1, 2, 3 or 4 heteroatoms independently selected from N, S and O. Monocyclic heteroaryls include, but are not limited to, furan, oxazole, thiophene, triazole, triazene, thiadiazole, oxadiazole, imidazole, isothiazole, isoxazole, pyrazole, pyridazine, pyridine, pyrazine, pyrimidine, pyrrole, tetrazole and thiazole. Bicyclic heteroaryls include, but are not limited to, indolizine, indole, isoindole, indazole, benzimidazole, benzothiazole, purine, quinoline, isoquinoline, cinnoline, phthalazine, quinazoline, quinoxaline, naphthyridine and pteridine.

"Heterocyclyl" refers to an optionally substituted, saturated or unsaturated, aliphatic or aromatic, monocyclic or polycyclic (e.g., bicyclic, tricyclic), monovalent, hydrocarbon ring system having the specified number of ring atoms, wherein at least one carbon atom in the ring system has been replaced with a heteroatom selected from N, S and O. Thus, "($C_3$-$C_8$)heterocyclyl" means a heterocyclic ring system having from 3-8 ring atoms. A heterocyclyl can be monocyclic, fused bicyclic, bridged bicyclic or polycyclic. A heterocyclyl can contain 1, 2, 3 or 4 heteroatoms independently selected from N, S and O. When one heteroatom is S, it can be optionally mono- or di-oxygenated (i.e., —S(O)— or —S(O)$_2$). A heterocyclyl can be saturated (i.e., contain no degree of unsaturation). In one embodiment, the heterocyclyl is a ($C_3$-$C_8$)heterocyclyl, in particular, a ($C_3$-$C_8$)saturated heterocyclyl. Alternatively, a heterocyclyl can be unsaturated (i.e., contain at least one degree of unsaturation, as in at least one double bond or triple bond) or aromatic (i.e., a heteroaryl).

Examples of monocyclic heterocyclyl include, but are not limited to, azetidine, pyrrolidine, piperidine, piperazine, azepane, tetrahydrofuran, tetrahydropyran, morpholine, thiomorpholine, dioxide, furan, oxazole, thiophene, triazole, triazene, thiadiazole, oxadiazole, imidazole, isothiazole, isoxazole, pyrazole, pyridazine, pyridine, pyrazine, pyrimidine, pyrrole, tetrazole and thiazole. Examples of monocyclic saturated heterocyclyl include, but are not limited to, azetidine, pyrrolidine, piperidine, piperazine, azepane, tetrahydrofuran, tetrahydropyran, morpholine, thiomorpholine, dioxide. Examples of fused bicyclic heterocyclyl include, but are not limited to, octahydrocyclopenta[c]pyrrolyl, indoline, isoindoline, 2,3-dihydro-1H-benzo[d]imidazole, 2,3-dihydrobenzo[d]oxazole, 2,3-dihydrobenzo[d]thiazole, indolizine, indole, isoindole, indazole, benzimidazole, benzothiazole, purine, quinoline, isoquinoline, cinnoline, phthalazine, quinazoline, quinoxaline, naphthyridine and pteridine. Examples of bridged bicyclic heterocyclyl include, but are not limited to, azabicyclononane and azabicyclooctane.

"Dialkylamino" means (alkyl)$_2$-N—, wherein the alkyl groups, which may be the same or different, are as described herein. Particular dialkylamino groups are (($C_1$-$C_5$)alkyl)$_2$-N—, wherein the alkyl groups may be the same or different. Dialkylamino includes, but is not limited to, dimethylamino, diethylamino and methylethylamino.

"Halogen" and "halo" are used interchangeably herein and each refers to fluorine, chlorine, bromine, or iodine. In some embodiments, halogen is selected from fluoro or chloro.

"Chloro" means —Cl.

"Fluoro" means —F.

"Carboxy" means —C(O)OH.

"Cyano" means —CN.

"Nitro" means —NO$_2$.

"Hydroxy" means —OH.

"Thio" means —SH.

"Alkoxy" refers to an alkyl radical attached through an oxygen linking atom, wherein alkyl is as described herein.

"Alkenoxy" refers to an alkenyl radical attached through an oxygen linking atom, wherein alkenyl is as described herein.

"Aryloxy" refers to an aryl radical attached through an oxygen linking atom, wherein aryl is as described herein.

"Cycloalkoxy" refers to a cycloalkyl radical attached through an oxygen linking atom, wherein cycloalkyl is as described herein.

"Heteroaryloxy" refers to a heteroaryl radical attached through an oxygen linking atom, wherein heteroaryl is as described herein.

"Heterocyclyloxy" refers to a heterocyclyl radical attached through an oxygen linking atom, wherein heterocyclyl is as described herein.

"Thioalkoxy" refers to an alkyl radical attached through a sulfur linking atom, wherein alkyl is as described herein.

"Haloalkyl" includes mono, poly, and perhaloalkyl groups, where each halogen is independently selected from fluorine, chlorine, and bromine and alkyl is as described herein. In one aspect, haloalkyl is perhaloalkyl (e.g., perfluoroalkyl). Haloalkyl includes, but is not limited to, trifluoromethyl and pentafluoroethyl.

"Hydroxyalkyl" includes mono, poly and perhydroxylated alkyl, where alkyl is as described herein. In a preferred aspect, hydroxyalkyl is monohydroxyalkyl. Hydroxyalkyl includes, but is not limited to, 2-hydroxyethyl, 2-hydroxypropyl and 3-hydroxypropyl.

"Haloalkoxy" refers to a haloalkyl radical attached through an oxygen linking atom, wherein haloalkyl is as described herein.

"Phosphate" means —OP(O)(OR)(OR'), wherein R and R' are independently selected from hydrogen or ($C_1$-$C_{10}$) alkyl, wherein the alkyl groups may be the same or different and alkyl is as described herein. In one aspect, R and R' are independently selected from hydrogen or ($C_1$-$C_5$)alkyl. Examples of phosphate include, but are not limited to, —H$_2$PO$_4$.

"Phosphonate" means —P(O)(OR)(OR'), wherein R and R' are independently selected from hydrogen or ($C_1$-$C_{10}$) alkyl, wherein the alkyl groups may be the same or different and alkyl is as described herein. In one aspect, R and R' are independently selected from hydrogen or ($C_1$-$C_5$)alkyl. Examples of phosphonate include, but are not limited to, —H$_2$PO$_3$.

"Sulfate" means —OS(O$_2$)(OR), wherein R is hydrogen or (C$_1$-C$_{10}$)alkyl and alkyl is as described herein. In one aspect, R is hydrogen or (C$_1$-C$_5$)alkyl. Examples of sulfate include, but are not limited to, —HSO$_4$ and —OSO$_3$CH$_3$.

"Sulfonyl" means —SO$_2$R, wherein R is hydrogen or (C$_1$-C$_{10}$)alkyl and alkyl is as described herein. In one aspect, R is hydrogen or (C$_1$-C$_5$)alkyl. Examples of sulfonyl include, but are not limited to, —SO$_2$H and —SO$_2$CH$_3$.

"Sulfonate" means —SO$_3$R, wherein R is hydrogen or (C$_1$-C$_{10}$)alkyl and alkyl is as described herein. In one aspect, R is hydrogen or (C$_1$-C$_5$)alkyl. Examples of sulfonate include, but are not limited to, —SO$_3$H and —SO$_3$CH$_3$.

"Sulfonamide" means —SO$_2$NRR', wherein R and R' are independently selected from hydrogen or (C$_1$-C$_{10}$)alkyl, wherein the alkyl groups may be the same or different and alkyl is as described herein. In one aspect, R and R' are independently selected from hydrogen or (C$_1$-C$_5$)alkyl. Examples of sulfonamide include, but are not limited to, —SO$_2$NH$_2$ and —SO$_2$N(CH$_3$)$_2$.

"Monosaccharide" refers to a simple sugar that cannot be hydrolyzed to give a simpler sugar. Monosaccharides are the building blocks of carbohydrates and typically, though not always, have the formula C$_x$(H$_2$O)$_y$, where x and y are greater than or equal to 3. Monosaccharides can be classified by the number of carbon atoms they contain. Thus, a triose contains three carbon atoms (i.e., x=3), a tetrose contains four carbon atoms (i.e., x=4), a pentose contains five carbon atoms (i.e., x=5) and a hexose contains six carbon atoms (i.e., x=6). Monosaccharides can be acyclic or cyclic. In some embodiments, the monosaccharide is acyclic. In a preferred embodiment, the monosaccharide is cyclic. Examples of pentoses include, but are not limited to, arabinose, lyxose, ribose, xylose, ribulose, xylulose, deoxyribose and fuculose. Examples of hexoses include, but are not limited to, allose, altrose, glucose, mannose, gulose, idose, galactose, talose, psicose, fructose, sorbose, tagatose, fucose and rhamnose.

It is understood that substituents on the compounds of the invention can be selected by one of ordinary skill in the art to provide compounds that are chemically stable and that can be readily synthesized by techniques known in the art, as well as those methods set forth below. The term "stable," as used herein, refers to compound that are not substantially altered when subjected to conditions to allow for their production, detection and, in certain embodiments, recovery, purification and use for one or more of the purposes disclosed herein.

Combinations of substituents (e.g., R$^1$-R$^4$, n, Ring A) envisioned by this invention are preferably those that result in the formation of stable or chemically feasible compounds. For example, it will be understood by one of ordinary skill in the art that the value for variable n in Structural Formulas I and II cannot exceed the number of substitutable positions on Ring A. Thus, when Ring A is phenyl, n cannot exceed 5. When Ring A is pyridinyl, n cannot exceed 4.

In general, the term "substituted," whether preceded by the term "optionally" or not, means that one or more hydrogens of the designated group are replaced with a suitable substituent. Unless otherwise indicated, an "optionally substituted group" can have a suitable substituent at each substitutable position of the group and, when more than one position in any given structure may be substituted with more than one substituent selected from a specified group, the substituent can be the same or different at every position. Alternatively, an "optionally substituted group" can be unsubstituted.

Suitable substituents on a substitutable carbon or nitrogen atom of an optionally substituted group include (C$_1$-C$_{10}$) alkyl, (C$_1$-C$_{10}$)alkylamino, (C$_1$-C$_{10}$)alkenyl, (C$_1$-C$_{10}$)alkenoxy, (C$_1$-C$_{10}$)alkoxy, (C$_1$-C$_{10}$)alkynyl, (C$_1$-C$_{10}$)acyl, (C$_1$-C$_{10}$)alkanoyl, amido, amino, formyl, (C$_6$-C$_{15}$)aryl, (C$_6$-C$_{15}$)aryloxy, carboxy, cyano, (C$_3$-C$_{15}$)cycloalkyl, (C$_3$-C$_{15}$)cycloalkoxy, (C$_1$-C$_{10}$)dialkylamino, (C$_1$-C$_{10}$)ether, halo(C$_1$-C$_{10}$)alkyl, halo(C$_1$-C$_{10}$)alkoxy, halogen, (C$_5$-C$_{13}$)heteroaryl, (C$_5$-C$_{15}$)heteroaryloxy, (C$_3$-C$_{15}$)heterocyclyl, (C$_3$-C$_{15}$)heterocyclyloxy, hydroxy, nitro, phosphate, phosphonate, sulfate, sulfonamide, sulfonyl, sulfonate, thio and thio(C$_1$-C$_{10}$) alkoxy. In some embodiments, suitable substituents on a substitutable carbon or nitrogen atom of an optionally substituted group include (C$_1$-C$_{10}$)alkyl, (C$_1$-C$_{10}$)alkylamino, (C$_1$-C$_{10}$)alkenyl, (C$_1$-C$_{10}$)alkenoxy, (C$_1$-C$_{10}$)alkoxy, (C$_1$-C$_{10}$)alkynyl, (C$_1$-C$_{10}$)acyl, (C$_1$-C$_{10}$)alkanoyl, amido, amino, formyl, (C$_6$)aryl, (C$_6$)aryloxy, carboxy, cyano, (C$_3$-C$_8$)cycloalkyl, (C$_3$-C$_8$)cycloalkoxy, (C$_1$-C$_{10}$)dialkylamino, (C$_1$-C$_{10}$)ether, halo(C$_1$-C$_{10}$)alkyl, halo(C$_1$-C$_{10}$)alkoxy, halogen, (C$_5$-C$_6$)heteroaryl, (C$_5$-C$_6$)heteroaryloxy, (C$_3$-C$_8$)heterocyclyl, (C$_3$-C$_8$)heterocyclyloxy, hydroxy, nitro, phosphate, phosphonate, sulfate, sulfonamide, sulfonyl, sulfonate, thio and thio(C$_1$-C$_{10}$)alkoxy. In some embodiments, suitable substituents on a substitutable carbon or nitrogen atom of an optionally substituted group include (C$_1$-C$_5$)alkyl, (C$_1$-C$_5$) alkylamino, (C$_1$-C$_5$)alkenyl, (C$_1$-C$_5$)alkenoxy, (C$_1$-C$_5$) alkoxy, (C$_1$-C$_5$)alkynyl, (C$_1$-C$_5$)acyl, (C$_1$-C$_5$)alkanoyl, amido, amino, formyl, (C$_6$)aryl, (C$_6$)aryloxy, carboxy, cyano, (C$_3$-C$_8$)cycloalkyl, (C$_3$-C$_8$)cycloalkoxy, (C$_1$-C$_5$)dialkylamino, (C$_1$-C$_5$)ether, halo(C$_1$-C$_5$)alkyl, halo(C$_1$-C$_5$) alkoxy, halogen, (C$_5$-C$_6$)heteroaryl, (C$_5$-C$_6$)heteroaryloxy, (C$_3$-C$_8$)heterocyclyl, (C$_3$-C$_8$)heterocyclyloxy, hydroxy, nitro, phosphate, phosphonate, sulfate, sulfonamide, sulfonyl, sulfonate, thio and thio(C$_1$-C$_5$)alkoxy. In some embodiments, suitable substituents on a substitutable carbon or nitrogen atom of an optionally substituted group include (C$_1$-C$_{10}$)alkyl, (C$_1$-C$_{10}$)alkylamino, (C$_1$-C$_{10}$)alkoxy, amido, amino, (C$_6$-C$_{15}$)aryl, (C$_6$-C$_{15}$)aryloxy, cyano, (C$_3$-C$_8$)cycloalkyl, (C$_3$-C$_8$)cycloalkoxy, (C$_1$-C$_{10}$)dialkylamino, halo (C$_1$-C$_{10}$)alkyl, halo(C$_1$-C$_{10}$)alkoxy, halogen, (C$_5$-C$_{15}$)heteroaryl, (C$_5$-C$_{15}$)heteroaryloxy, (C$_3$-C$_8$)heterocyclyl, (C$_3$-C$_8$)heterocyclyloxy, hydroxy, nitro, thio and thio(C$_1$-C$_{10}$) alkoxy. In some embodiments, suitable substituents on a substitutable carbon or nitrogen atom of an optionally substituted group include (C$_1$-C$_5$)alkylamino, (C$_1$-C$_5$)alkoxy, amino, cyano, (C$_1$-C$_5$)dialkylamino, halo(C$_1$-C$_5$)alkoxy, halogen, hydroxy, nitro, thio and thio(C$_1$-C$_5$)alkoxy. In some embodiments, suitable substituents on a substitutable carbon or nitrogen atom of an optionally substituted group include (C$_1$-C$_5$)alkoxy, halo(C$_1$-C$_5$)alkoxy, halogen, hydroxy, thio and thio(C$_1$-C$_5$)alkoxy. In some embodiments, suitable substituents on a substitutable carbon or nitrogen atom of an optionally substituted group include hydroxy, halogen, cyano, nitro, thio, amino, (C$_1$-C$_5$)alkylamino, (C$_1$-C$_5$)dialkylamino, sulfonyl, sulfonate, sulfonamide, sulfate, formyl, (C$_1$-C$_5$)acyl, (C$_1$-C$_5$)alkanoyl, amido, carboxy, (C$_1$-C$_5$) alkoxy, thio(C$_1$-C$_5$)alkoxy, phosphate and phosphonate. In some embodiments, suitable substituents on a substitutable carbon or nitrogen atom of an optionally substituted group include hydroxy, halogen, thio, amino, sulfonyl, sulfonate, sulfonamide, —NH$_2$, carboxy, phosphate and phosphonate.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds described herein include salts derived from suitable inorganic and organic acids and bases that are compatible with the treatment of subjects.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms.

In some embodiments, acid addition salts are most suitably formed from pharmaceutically acceptable acids, and include, for example, those formed with inorganic acids, e.g., hydrochloric, sulfuric or phosphoric acids and organic acids, e.g., succinic, maleic, acetic or fumaric acid.

Illustrative inorganic bases which form suitable salts include, but are not limited to, lithium, sodium, potassium, calcium, magnesium or barium hydroxides. Illustrative organic bases which form suitable salts include aliphatic, alicyclic or aromatic organic amines, such as methylamine, trimethyl amine and picoline, or ammonia. The selection criteria for the appropriate salt will be known to one skilled in the art.

Salts derived from appropriate bases include alkali metal, alkaline earth metal, ammonium and $N^+((C_1-C_4)alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this invention. Such compounds are useful, for example, as analytical tools, as probes in biological assays, or as therapeutic agents in accordance with the present invention.

When introducing elements disclosed herein, the articles "a," "an," "the," and "said" are intended to mean that there are one or more of the elements. The terms "comprising," "having" and "including" are intended to be open-ended and mean that there may be additional elements other than the listed elements.

Compounds

A first embodiment is a compound represented by Structural Formula I:

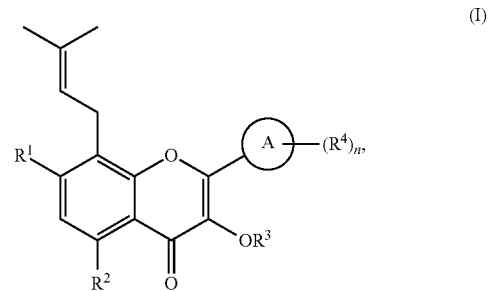

or a pharmaceutically acceptable salt thereof, wherein:
$R^1$ is —O-monosaccharide, hydroxy, hydrogen, halogen or carboxy or optionally substituted —C(O)O(C$_1$-C$_{10}$)alkyl, —C(O)O(C$_1$-C$_{10}$)alkenyl or —C(O)O(C$_1$-C$_{10}$)alkynyl;
$R^2$ is hydroxy, —O-monosaccharide, hydrogen, halogen or optionally substituted (C$_1$-C$_{10}$)alkoxy;
$R^3$ is optionally substituted (C$_1$-C$_5$)alkyl (e.g., C$_1$, C$_2$, C$_3$, C$_4$, C$_5$ alkyl);
Ring A is a (C$_3$-C$_{15}$)unsaturated or aromatic carbocyclyl or a (C$_3$-C$_{15}$)unsaturated or aromatic heterocyclyl;
each $R^4$ is independently (C$_1$-C$_{10}$)alkyl, (C$_1$-C$_{10}$)alkylamino, (C$_1$-C$_{10}$)alkenyl, (C$_1$-C$_{10}$)alkenoxy, (C$_1$-C$_{10}$)alkoxy, (C$_1$-C$_{10}$)alkynyl, (C$_1$-C$_{10}$)acyl, (C$_1$-C$_{10}$)alkanoyl, amido, amino, formyl, (C$_6$-C$_{15}$)aryl, (C$_6$-C$_{15}$)aryloxy, carboxy, cyano, (C$_3$-C$_{15}$)cycloalkyl, (C$_3$-C$_{15}$)cycloalkoxy, (C$_1$-C$_{10}$)dialkylamino, (C$_1$-C$_{10}$)ether, halo(C$_1$-C$_{10}$)alkyl, halo(C$_1$-C$_{10}$)alkoxy, halogen, (C$_5$-C$_{13}$)heteroaryl, (C$_5$-C$_{15}$)heteroaryloxy, (C$_3$-C$_{15}$)heterocyclyl, (C$_3$-C$_{15}$)heterocyclyloxy, hydroxy, nitro, phosphate, phosphonate, sulfate, sulfonyl, sulfonamide, sulfonate, thio or thio(C$_1$-C$_{10}$)alkoxy; and
n is 0, 1, 2, 3, 4, 5, 6, 7, 8, 9, 10, 11, 12, 13 or 14.

In a first aspect of the first embodiment, $R^1$ is —O-monosaccharide, hydroxy or hydrogen (e.g., —O-monosaccharide or hydroxy). Values for the remaining variables are as described in the first embodiment.

In a second aspect of the first embodiment, $R^1$ is —O-monosaccharide (e.g., a pentose or a hexose). Values for the remaining variables are as described in the first embodiment, or first aspect thereof.

In a third aspect of the first embodiment, $R^1$ is a hexose. Values for the remaining variables are as described in the first embodiment, or first or second aspect thereof.

In a fourth aspect of the first embodiment, $R^1$ is selected from allose, altrose, glucose, mannose, gulose, idose, galactose, talose, psicose, fructose, sorbose, tagatose, fucose or rhamnose. Values for the remaining variables are as described in the first embodiment, or first through third aspects thereof.

In a fifth aspect of the first embodiment, $R^1$ is glucose. Values for the remaining variables are as described in the first embodiment, or first through fourth aspects thereof.

In a sixth aspect of the first embodiment, $R^1$ is hydroxy. Values for the remaining variables are as described in the first embodiment, or first through fifth aspects thereof.

In a seventh aspect of the first embodiment, $R^2$ is hydroxy, —O-monosaccharide, $(C_1-C_{10})$alkoxy or halo$(C_1-C_{10})$alkoxy (e.g., hydroxy). Values for the remaining variables are as described in the first embodiment, or first through sixth aspects thereof.

In an eighth aspect of the first embodiment, $R^2$ is hydroxy, —O-monosaccharide or hydrogen. Values for the remaining variables are as described in the first embodiment, or first through seventh aspects thereof.

In a ninth aspect of the first embodiment, $R^3$ is hydroxymethyl, hydroxylethyl, hydroxypropyl, hydroxybutyl or hydroxypentyl (e.g., hydroxyethyl or hydroxypropyl). Values for the remaining variables are as described in the first embodiment, or first through eighth aspects thereof.

In a tenth aspect of the first embodiment, $R^3$ is 2-hydroxyethyl, 3-hydroxypropyl or 2-hydroxypropyl. Values for the remaining variables are as described in the first embodiment, or first through ninth aspects thereof.

In an eleventh aspect of the first embodiment, n is 0, 1, 2, 3, 4 or 5 (e.g., 0, 1, 2, 3, or 4; 0, 1, 2 or 3; 0, 1 or 2; 1; 2; or 3). Values for the remaining variables are as described in the first embodiment, or first through tenth aspects thereof.

In a twelfth aspect of the first embodiment, Ring A is a $(C_6-C_{15})$aryl or a $(C_5-C_{15})$heteroaryl. Values for the remaining variables are as described in the first embodiment, or first through eleventh aspects thereof.

In a thirteenth aspect of the first embodiment, Ring A is a five-membered heteroaryl and n is 0, 1, 2, 3 or 4; or Ring A is a six-membered heteroaryl and n is 0, 1, 2, 3, 4 or 5. Values for the remaining variables and alternative values for n are as described in the first embodiment, or first through twelfth aspects thereof.

In a fourteenth aspect of the first embodiment, Ring A is phenyl and n is 0, 1, 2, 3, 4 or 5. Values for the remaining variables and alternative values for n are as described in the first embodiment, or first through thirteenth aspects thereof.

In a fifteenth aspect of the first embodiment, each monosaccharide is independently selected from a pentose and a hexose. In a first aspect of the fifteenth aspect of the first embodiment, each pentose is independently selected from arabinose, lyxose, ribose, xylose, ribulose, xylulose, deoxyribose or fuculose. In a second aspect of the fifteenth aspect of the first embodiment or an aspect of the first aspect of the fifteenth aspect of the first embodiment, each hexose is independently selected from allose, altrose, glucose, mannose, gulose, idose, galactose, talose, psicose, fructose, sorbose, tagatose, fucose or rhamnose. Values for the remaining variables are as described in the first embodiment, or first through fourteenth aspects thereof.

In a sixteenth aspect of the first embodiment, $R^1$ is —O-monosaccharide, hydroxy, hydrogen, halogen or carboxy, or —C(O)O($C_1-C_{10}$)alkyl, —C(O)O($C_1-C_{10}$)alkenyl or —C(O)O($C_1-C_{10}$)alkynyl optionally substituted with one or more substituents independently selected from $(C_1-C_5)$alkylamino, $(C_1-C_5)$alkoxy, amino, cyano, $(C_1-C_5)$dialkylamino, halo$(C_1-C_5)$alkoxy, halogen, hydroxy, nitro, thio or thio$(C_1-C_5)$alkoxy. Values for the remaining variables and alternative values for $R^1$ are as described in the first embodiment, or first through fifteenth aspects thereof.

In a seventeenth aspect of the first embodiment, $R^2$ is hydroxy, —O-monosaccharide, hydrogen, halogen or $(C_1-C_{10})$alkoxy optionally substituted with one or more substituents independently selected from $(C_1-C_5)$alkylamino, $(C_1-C_5)$alkoxy, amino, cyano, $(C_1-C_5)$dialkylamino, halo$(C_1-C_5)$alkoxy, halogen, hydroxy, nitro, thio or thio$(C_1-C_5)$alkoxy. Values for the remaining variables and alternative values for $R^2$ are as described in the first embodiment, or first through sixteenth aspects thereof.

In an eighteenth aspect of the first embodiment, $R^3$ is $(C_1-C_5)$alkyl substituted with at least one substituent selected from hydroxy, halogen, cyano, nitro, thio, amino, $(C_1-C_5)$alkylamino, $(C_1-C_5)$dialkylamino, sulfonyl, sulfonate, sulfate, formyl, $(C_1-C_5)$acyl, $(C_1-C_5)$alkanoyl, amido, carboxy, $(C_1-C_5)$alkoxy, thio$(C_1-C_5)$alkoxy, phosphate or phosphonate. Values for the remaining variables and alternative values for $R^3$ are as described in the first embodiment, or first through seventeenth aspects thereof.

In a nineteenth aspect of the first embodiment, each $R^4$ is independently $(C_1-C_{10})$alkyl, $(C_1-C_{10})$alkylamino, $(C_1-C_{10})$alkenyl, $(C_1-C_{10})$alkenoxy, $(C_1-C_{10})$alkoxy, $(C_1-C_{10})$alkynyl, $(C_1-C_{10})$acyl, $(C_1-C_{10})$alkanoyl, amido, amino, formyl, $(C_6)$aryl, $(C_6)$aryloxy, carboxy, cyano, $(C_3-C_8)$cycloalkyl, $(C_3-C_8)$cycloalkoxy, $(C_1-C_{10})$dialkylamino, $(C_1-C_{10})$ether, halo$(C_1-C_{10})$alkyl, halo$(C_1-C_{10})$alkoxy, halogen, $(C_5-C_6)$heteroaryl, $(C_5-C_6)$heteroaryloxy, $(C_3-C_8)$heterocyclyl, $(C_3-C_8)$heterocyclyloxy, hydroxy, nitro, phosphate, phosphonate, sulfate, sulfonyl, sulfonamide, sulfonate, thio or thio$(C_1-C_{10})$alkoxy. Values for the remaining variables are as described in the first embodiment, or first through eighteenth aspects thereof.

In a twentieth aspect of the first embodiment, each $R^4$ is independently $(C_1-C_5)$alkyl, $(C_1-C_5)$alkylamino, $(C_1-C_5)$alkenyl, $(C_1-C_5)$alkenoxy, $(C_1-C_5)$alkoxy, $(C_1-C_5)$alkynyl, $(C_1-C_5)$acyl, $(C_1-C_5)$alkanoyl, amido, amino, formyl, $(C_6)$aryl, $(C_6)$aryloxy, carboxy, cyano, $(C_3-C_8)$cycloalkyl, $(C_3-C_8)$cycloalkoxy, $(C_1-C_5)$dialkylamino, $(C_1-C_5)$ether, halo$(C_1-C_5)$alkyl, halo$(C_1-C_5)$alkoxy, halogen, $(C_5-C_6)$heteroaryl, $(C_5-C_6)$heteroaryloxy, $(C_3-C_8)$heterocyclyl, $(C_3-C_8)$heterocyclyloxy, hydroxy, nitro, phosphate, phosphonate, sulfate, sulfonyl, sulfonamide, sulfonate, thio or thio$(C_1-C_5)$alkoxy. Values for the remaining variables are as described in the first embodiment, or first through nineteenth aspects thereof.

In a twenty-first aspect of the first embodiment, each $R^4$ is independently $(C_1-C_{10})$alkyl, $(C_1-C_{10})$alkylamino, $(C_1-C_{10})$alkoxy, amido, amino, $(C_6-C_{15})$aryl, $(C_6-C_{15})$aryloxy, cyano, $(C_3-C_8)$cycloalkyl, $(C_3-C_8)$cycloalkoxy, $(C_1-C_{10})$dialkylamino, halo$(C_1-C_{10})$alkyl, halo$(C_1-C_{10})$alkoxy, halogen, $(C_5-C_{15})$heteroaryl, $(C_5-C_{15})$heteroaryloxy, $(C_3-C_8)$heterocyclyl, $(C_3-C_8)$heterocyclyloxy, hydroxy, nitro, thio or thio$(C_1-C_{10})$alkoxy. Values for the remaining variables are as described in the first embodiment, or first through twentieth aspects thereof.

In a twenty-second aspect of the first embodiment, each $R^4$ is independently $(C_1-C_5)$alkylamino, $(C_1-C_5)$alkoxy, amino, cyano, $(C_1-C_5)$dialkylamino, halo$(C_1-C_5)$alkoxy, halogen, hydroxy, nitro, thio or thio$(C_1-C_5)$alkoxy (e.g., methoxy). Values for the remaining variables are as described in the first embodiment, or first through twenty-first aspects thereof.

In a twenty-third aspect of the first embodiment, each $R^4$ is independently $(C_1-C_5)$alkoxy (e.g., methoxy), halo$(C_1$-

$C_5$)alkoxy, halogen, hydroxy, thio or thio($C_1$-$C_5$)alkoxy (e.g., methoxy, trifluoromethoxy, fluoro, chloro, bromo or hydroxy). Values for the remaining variables are as described in the first embodiment, or first through twenty-second aspects thereof.

In a twenty-fourth aspect of the first embodiment, each $R^4$ is independently hydroxy, halogen, cyano, nitro, thio, amino, ($C_1$-$C_5$)alkylamino, ($C_1$-$C_5$)dialkylamino, sulfonyl, sulfonate, sulfonamide, sulfate, formyl, ($C_1$-$C_5$)acyl, ($C_1$-$C_5$)alkanoyl, amido, carboxy, ($C_1$-$C_5$)alkoxy, thio($C_1$-$C_5$)alkoxy, phosphate or phosphonate. Values for the remaining variables are as described in the first embodiment, or first through twenty-third aspects thereof.

In a twenty-fifth aspect of the first embodiment, each $R^4$ is independently hydroxy, halogen, thio, amino, sulfonyl, sulfonate, sulfonamide, —$NH_2$, carboxy, phosphate or phosphonate. Values for the remaining variables are as described in the first embodiment, or first through twenty-fourth aspects thereof.

In a twenty-sixth aspect of the first embodiment, $R^3$ is ($C_1$-$C_5$)alkyl substituted with at least one substituent selected from hydroxy, halogen, thio, amino, sulfonyl, sulfonate, sulfonamide, —$NH_2$, carboxy, phosphate or phosphonate. Values for the remaining variables are as described in the first embodiment, or first through twenty-fifth aspects thereof.

In a twenty-seventh aspect of the first embodiment, $R^3$ is ($C_1$-$C_5$)hydroxyalkyl. Values for the remaining variables are as described in the first embodiment, or first through twenty-sixth aspects thereof.

A second embodiment is a compound represented by Structural Formula II:

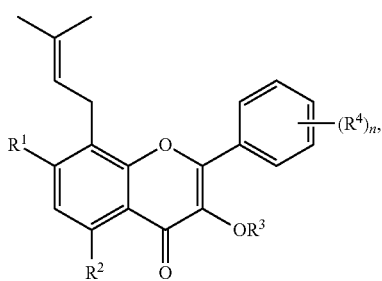

(II)

or a pharmaceutically acceptable salt thereof, wherein n is 0, 1, 2, 3, 4 or 5. Values for the remaining variables and alternative values for variable n are as described in the first embodiment, or any aspect thereof.

A third embodiment is a compound represented by Structural Formula (III):

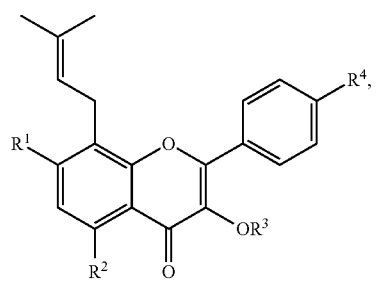

(III)

or a pharmaceutically acceptable salt thereof. Values for the variables are as described in the first embodiment, or any aspect thereof, or the second embodiment.

Compounds of Structural Formulas I-III include compounds 3-8 in Table 1, or a pharmaceutically acceptable salt of any of the foregoing.

Compositions

Provided herein is a composition (e.g., a pharmaceutically acceptable composition) comprising a compound disclosed herein (e.g., a compound of any of Structural Formulas I-III, or a pharmaceutically acceptable salt of any of the foregoing), and a pharmaceutically acceptable carrier or excipient. In certain embodiments, a composition of the invention is formulated for administration to a subject (e.g., a patient) in need of the composition. In some embodiments, a composition of the invention is formulated for oral, intravenous, subcutaneous, intraperitoneal or dermatological administration to a subject in need thereof.

The phrase "pharmaceutically acceptable carrier or excipient" refers to a non-toxic carrier or excipient that does not destroy the pharmacological activity of the agent with which it is formulated and is nontoxic when administered in doses sufficient to deliver a therapeutic amount of the agent. Pharmaceutically acceptable carriers or excipients that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally (including subcutaneously, intramuscularly, intravenously and intradermally), by inhalation spray, topically, rectally, nasally, buccally, vaginally or via an implanted reservoir. In some embodiments, provided compounds or compositions are administrable intravenously and/or intraperitoneally.

The term "parenteral," as used herein, includes subcutaneous, intracutaneous, intravenous, intramuscular, intraocular, intravitreal, intra-articular, intra-arterial, intra-synovial, intrasternal, intrathecal, intralesional, intrahepatic, intraperitoneal intralesional and intracranial injection or infusion techniques. Preferably, the compositions are administered orally, subcutaneously, intraperitoneally or intravenously.

Compositions provided herein can be orally administered in any orally acceptable dosage form including, but not limited to, capsules, tablets, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some embodiments, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders, such as carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium salts, (g) wetting agents, such as acetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

A compound described herein can also be in microencapsulated form with one or more excipients, as noted above. In such solid dosage forms, the compound can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Compositions for oral administration may be designed to protect the active ingredient against degradation as it passes through the alimentary tract, for example, by an outer coating of the formulation on a tablet or capsule.

In another embodiment, a compound described herein can be provided in an extended (or "delayed" or "sustained") release composition. This delayed-release composition comprises the compound in combination with a delayed-release component. Such a composition allows targeted release of a provided agent into the lower gastrointestinal tract, for example, into the small intestine, the large intestine, the colon and/or the rectum. In certain embodiments, a delayed-release composition further comprises an enteric or pH-dependent coating, such as cellulose acetate phthalates and other phthalates (e.g., polyvinyl acetate phthalate, methacrylates (Eudragits)). Alternatively, the delayed-release composition provides controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/or by acrylic acid linked to azoaromatic bonds coatings.

Compositions described herein can also be administered in the form of suppositories for rectal administration. These can be prepared by mixing a compound described herein with a suitable non-irritating excipient that is solid at room temperature but liquid at rectal temperature and, therefore, will melt in the rectum to release the drug. Such materials include cocoa butter, beeswax and polyethylene glycols.

Compositions described herein can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For other topical applications, the compositions can be formulated in a suitable ointment containing the active component suspended or dissolved in one or more carriers. Carriers for topical administration of a compound described herein include, but are not limited to, mineral oil, liquid petrolatum, white petrolatum, propylene glycol, polyoxyethylene, polyoxypropylene compound, emulsifying wax and water and penetration enhancers. Alternatively, compositions can be formulated in a suitable lotion or cream containing the active compound suspended or dissolved in one or more pharmaceutically acceptable carriers. Alternatively, the composition can be formulated with a suitable lotion or cream containing the active compound suspended or dissolved in a carrier with suitable emulsifying agents. In some embodiments, suitable carriers include, but are not limited to, mineral oil, sorbitan monostearate, polysorbate 60, cetyl esters wax, cetearyl alcohol, 2-octyldodecanol, benzyl alcohol and water. In other embodiments, suitable carriers include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic use, the compositions can be formulated in an ointment such as petrolatum.

Compositions can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

The amount of a compound described herein that can be combined with the carrier materials to produce a composition in a single dosage form will vary depending upon the host treated, the particular mode of administration and the activity of the agent employed. Preferably, compositions should be formulated so that a dosage of from about 0.01 mg/kg to about 100 mg/kg body weight/day of the agent can be administered to a subject receiving the composition.

It should also be understood that a specific dosage and treatment regimen for any particular patient will depend upon a variety of factors, including the activity of the specific agent employed, the age, body weight, general health, sex, diet, time of administration, rate of excretion, drug combination, the judgment of the treating physician and the severity of the particular disease being treated. The amount of a compound in the composition will also depend upon the particular compound in the composition.

Other pharmaceutically acceptable carriers, adjuvants and vehicles that can be used in the compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of agents described herein.

The compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

In some embodiments, compositions comprising a compound described herein (e.g., a compound of any of Structural Formulas I-III, or a pharmaceutically acceptable salt of any of the foregoing) can also include one or more other therapeutic agents. When the compositions of this invention comprise a combination of a compound described herein and one or more other therapeutic agents, the agents should be present at dosage levels of between about 1 to 100%, and more preferably between about 5% to about 95% of the dosage normally administered in a monotherapy regimen. The additional agent(s) can be part of a single dosage form, mixed together with the compound described herein in a single composition. Alternatively, the additional agent(s) can be administered separately, as part of a multiple dose regimen, from the compound described herein.

Thus, also provided is a kit comprising a compound described herein (e.g., a compound of any of Structural Formulas I-III, or a pharmaceutically acceptable salt of any of the foregoing) and an additional agent(s). In one embodiment, the kit comprises an effective amount of a compound described herein to treat a disease, disorder or condition described herein, and an effective amount of an additional agent(s) to treat a disease, disorder or condition described herein).

The compositions described herein can, for example, be administered by injection, intravenously, intraarterially, intraocularly, intravitreally, subdermally, orally, buccally, nasally, transmucosally, topically, in an ophthalmic preparation, or by inhalation, with a dosage ranging from about 0.5 mg/kg to about 100 mg/kg of body weight or, alternatively, in a dosage ranging from about 1 mg/dose to about 1000 mg/dose, every 4 to 120 hours, or according to the requirements of the particular drug. Typically, the compositions will be administered from about 1 to about 6 (e.g., 1, 2, 3, 4, 5 or 6) times per day or, alternatively, as a continuous infusion. The amount of active ingredient that can be combined with a carrier material to produce a single dosage form will vary depending upon the host treated and the particular mode of administration. A typical preparation will contain from about 5% to about 95% active compound (w/w). Alternatively, a preparation can contain from about 20% to about 80% active compound (w/w).

Doses lower or higher than those recited above may be required. Specific dosage and treatment regimens for any particular patient will depend upon a variety of factors, including the activity of the specific agent employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a subject's condition, a maintenance dose of a compound (e.g., a compound of any of Structural Formulas I-III, or a pharmaceutically acceptable salt of any of the foregoing), composition or combination of this invention can be administered, if necessary. Subsequently, the dosage or frequency of administration, or both, can be reduced, as a function of the symptoms, to a level at which the improved condition is retained when the symptoms have been alleviated to the desired level. Subjects may, however, require intermittent treatment on a long-term basis upon recurrence of disease symptoms.

Methods

Provided herein is a method of treating a PDE5-mediated disease in a subject in need thereof, comprising administering to the subject an effective amount of a compound described herein (e.g., a compound of any of Structural Formulas I-III, or a pharmaceutically acceptable salt of any of the foregoing) or a composition comprising an effective amount of a compound described herein (e.g., a compound of any of Structural Formulas I-III, or a pharmaceutically acceptable salt of any of the foregoing). As used herein, "PDE5-mediated disease" refers to any disease or other deleterious disorder or condition in which PDE5 plays a role. PDE5-mediated diseases include, but are not limited to, cardiovascular, gastrointestinal, pulmonary, musculoskeletal, neurological and reproductive diseases, disorders and conditions, such as those described herein.

Also provided herein is a method of treating a cardiovascular, gastrointestinal, pulmonary, musculoskeletal, neurological or reproductive disease, disorder or condition in a subject in need thereof, comprising administering to the subject an effective amount of a compound described herein (e.g., a compound of any of Structural Formulas I-III, or a pharmaceutically acceptable salt of any of the foregoing) or a composition comprising an effective amount of a compound described herein (e.g., a compound of any of Structural Formulas I-III, or a pharmaceutically acceptable salt of any of the foregoing).

In some embodiments, the disease, disorder or condition is a cardiovascular disease, disorder or condition. Examples of cardiovascular disease, disorders or conditions include, but are not limited to, heart disease (e.g., valvular, congenital, rheumatic, endocarditis, myocarditis), heart attack, arrhythmia, angina, hypertension, heart failure (e.g., congestive heart failure), stroke, peripheral vascular disease, atherosclerosis and preeclampsia.

In some embodiments, the disease, disorder or condition is a gastrointestinal disease, disorder or condition. Examples of gastrointestinal disease, disorders or conditions include, but are not limited to, gastritis, gastroenteritis and inflammatory bowel disease (e.g., Crohn's disease, ulcerative colitis).

In some embodiments, the disease, disorder or condition is a pulmonary disease, disorder or condition. Examples of pulmonary disease, disorders or conditions include, but are not limited to, pulmonary hypertension, asthma (e.g., chronic asthma, allergic asthma), chronic obstructive pulmonary disease (COPD), emphysema, bronchitis (e.g., chronic bronchitis, acute bronchitis), allergic rhinitis and cystic fibrosis.

In some embodiments, the disease, disorder or condition is a musculoskeletal disease, disorder or condition. Examples of musculoskeletal disease, disorders or conditions include, but are not limited to, carpal tunnel syndrome, tendonitis, tension neck syndrome, muscle strain, tendon strain, thoracic outlet compression, epicondylitis, radial tunnel syndrome, digital neuritis, trigger finger, DeQuervain's syndrome, mechanical back syndrome, degenerative disc disease, ruptured/herniated disc and degenerative muscle diseases such as Duchenne muscular dystrophy.

In some embodiments, the disease, disorder or condition is a neurological disease, disorder or condition. Examples of neurological disease, disorders or conditions include, but are not limited to, Amyotrophic Lateral Sclerosis (ALS), Huntington's Disease (HD), Parkinson's Disease (PD), Spinal Muscular Atrophy (SMA), Alzheimer's Disease (AD), diffuse Lewy body dementia (DLBD), multiple system atrophy (MSA), dystrophia myotonica, dentatorubro-pallidoluysian atrophy (DRPLA), Friedreich's ataxia, fragile X syndrome, fragile XE mental retardation, Machado-Joseph Disease (MJD or SCA3), spinobulbar muscular atrophy (also known as Kennedy's Disease), spinocerebellar ataxia type 1 (SCA1), spinocerebellar ataxia type 2 (SCA2), spinocerebellar ataxia type 6 (SCA6), spinocerebellar ataxia type 7 (SCAT), spinocerebellar ataxia type 17 (SCA17), chronic liver diseases, familial encephalopathy with neuroserpin inclusion bodies (FENIB), Pick's disease, corticobasal degeneration (CBD), progressive supranuclear palsy (PSP), amyotrophic lateral sclerosis/parkinsonism dementia complex, cataract, serpinopathies, haemolytic anemia, cystic fibrosis, Wilson's Disease, neurofibromatosis type 2, demyelinating peripheral neuropathies, retinitis pigmentosa, Marfan syndrome, emphysema, idiopathic pulmonary fibrosis, Argyophilic grain dementia, corticobasal degeneration, diffuse neurofibrillary tangles with calcification, frontotemporal dementia/parkinsonism linked to chromosome 17, Hallervorden-Spatz disease, NiemanPick disease type C, subacute sclerosing panencephalitis, cognitive disorders including dementia (e.g., associated with Alzheimer's disease, ischemia, trauma, vascular problems or stroke, HIV disease, Parkinson's disease, Huntington's disease, Pick's disease, Creutzfeldt-Jakob disease, perinatal hypoxia, other general medical conditions or substance abuse), delirium, amnestic disorders or age related cognitive decline, anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition, schizophrenia or psychosis including schizophrenia (e.g., paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder, substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics), movement disorders, including akinesias and akinetic-rigid syndromes (including Parkinson's disease, drug-induced parkinsonism, postencephalitic parkinsonism, progressive supranuclear palsy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tics), and dystonia (including generalized dystonia such as iodiopathic dystonia, drug-induced dystonia, symptomatic dystonia and paroxysmal dystonia, and focal dystonia such as blepharospasm, oromandibular dystonia, spasmodic dysphonia, spasmodic torticollis, axial dystonia, dystonic writer's cramp and hemiplegic dystonia), obesity, bulimia nervosa and compulsive eating disorders, pain including bone and joint pain (osteoarthritis), repetitive motion pain, dental pain, cancer pain, myofascial pain (muscular injury, fibromyalgia), perioperative pain (general surgery, gynecological), chronic pain, neuropathic pain, posttraumatic pain, trigeminal neuralgia, migraine and migraine headache, obesity or eating disorders associated with excessive food intake and complications associated therewith, attention-deficit/hyperactivity disorder, conduct disorder, mood disorders including depressive disorders, bipolar disorders, mood disorders due to a general medical condition and substance-induced mood disorders, muscular spasms and disorders associated with muscular spasticity or weakness including tremors, urinary incontinence, neuronal damage including ocular damage, retinopathy or macular degeneration of the eye, hearing loss or tinnitus, emesis, brain edema and sleep disorders including narcolepsy, and apoptosis of motor neuron cells. Illustrative examples of neuropathic pain include diabetic polyneuropathy, entrapment neuropathy, phantom pain, thalamic pain after stroke, post-herpetic neuralgia, atypical facial neuralgia pain after tooth extraction and the like, spinal cord injury, trigeminal neuralgia and cancer pain resistant to narcotic analgesics such as morphine. Neuropathic pain includes the pain caused by either central or peripheral nerve damage, and it includes the pain caused by either mononeuropathy or polyneuropathy.

In some embodiments, the disease, disorder or condition is a reproductive disease, disorder or condition. An example of a reproductive disease, disorder or condition is erectile dysfunction.

Also provided herein is a method of treating cancer in a subject in need thereof, comprising administering to the subject an effective amount of a compound described herein (e.g., a compound of any of Structural Formulas I-III, or a pharmaceutically acceptable salt of any of the foregoing) or a composition comprising an effective amount of a compound described herein (e.g., a compound of any of Structural Formulas I-III, or a pharmaceutically acceptable salt of any of the foregoing). The cancer can be a solid tumor, a leukemia, a lymphoma or a myeloma. In particular embodiments, the subject in need thereof has a breast cancer, a colon cancer, a lung cancer, a pancreatic cancer, a prostate cancer, a bone cancer, a blood cancer, a brain cancer, or a liver cancer.

Cancers include, but are not limited to: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Mantle Cell Lymphoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

Metastases of the aforementioned cancers can also be treated in accordance with the methods described herein.

Also provided herein is a method of treating osteoporosis or bone fracture in a subject in need thereof, comprising administering to the subject an effective amount of a compound described herein (e.g., a compound of any of Structural Formulas I-III, or a pharmaceutically acceptable salt of any of the foregoing) or a composition comprising an effective amount of a compound described herein (e.g., a compound of any of Structural Formulas I-III, or a pharmaceutically acceptable salt of any of the foregoing).

Also provided herein is a method of treating an inflammatory or autoimmune disorder in a subject in need thereof, comprising administering to the subject an effective amount of a compound described herein (e.g., a compound of any of Structural Formulas I-III, or a pharmaceutically acceptable salt of any of the foregoing) or a composition comprising an effective amount of a compound described herein (e.g., a compound of any of Structural Formulas I-III, or a pharmaceutically acceptable salt of any of the foregoing). Examples of inflammatory and autoimmune disorders include, but are not limited to, systemic lupus erythematosus, Hashimoto's disease, rheumatoid arthritis, gouty arthritis, graft-versus-host disease, Sjogren's syndrome, pernicious anemia, Addison disease, scleroderma, Goodpasture's syndrome, inflammatory bowel diseases such as Crohn's disease, colitis (e.g., atypical colitis, chemical colitis, collagenous colitis, distal colitis, diversion colitis, fulminant colitis, indeterminate colitis, infectious colitis, ischemic colitis, lymphocytic colitis, microscopic colitis), gastroenteritis, Hirschsprung's disease, Morbus Crohn, non-chronic or chronic digestive diseases, non-chronic or chronic inflammatory digestive diseases, regional enteritis and ulcerative colitis, autoimmune hemolytic anemia, sterility, myasthenia gravis, multiple sclerosis, Basedow's disease, thrombopenia purpura, insulin-dependent diabetes mellitus, allergy, asthma, atopic disease, arteriosclerosis, myocarditis, cardiomyopathy, glomerular nephritis, hypoplastic anemia, rejection after organ transplantation and numerous malignancies of lung, prostate, liver, ovary, colon, cervix, lymphatic and breast tissues, psoriasis, acne vulgaris, asthma, celiac disease, chronic prostatitis, glomerulonephritis, pelvic inflammatory disease, reperfusion injury sarcoidosis, vasculitis, interstitial cystitis, type 1 hypersensitivities, systemic sclerosis, dermatomyositis, polymyositis, and inclusion body myositis.

Also provided herein is a method of lowering cholesterol (e.g., as by lowering lipids) in a subject in need thereof, comprising administering to the subject an effective amount of a compound described herein (e.g., a compound of any of Structural Formulas I-III, or a pharmaceutically acceptable salt of any of the foregoing) or a composition comprising an effective amount of a compound described herein (e.g., a compound of any of Structural Formulas I-III, or a pharmaceutically acceptable salt of any of the foregoing).

As used herein, the terms "treat," "treating," or "treatment," mean to counteract a medical condition to the extent that the medical condition is improved according to a clinically-acceptable standard.

In an embodiment, the subject (e.g., patient) is a mammal (e.g., human, non-human primate, cow, sheep, goat, horse, dog, cat, rabbit, guinea pig, rat, mouse or other bovine, ovine, equine, canine, feline, or rodent organism). In a particular embodiment, the subject is a human. A "subject in need thereof" refers to a subject who has, or is at risk for developing, a disease or condition described herein (e.g., a PDE5-mediated disease). A skilled medical professional (e.g., physician) can readily determine whether a subject has, or is at risk for developing, a disease or condition described herein (e.g., a PDE5-mediated disease).

In some embodiments, the subject has a PDE5-mediated disease, disorder or condition. In some embodiments, the subject has a cardiovascular, gastrointestinal, pulmonary, musculoskeletal, neurological or reproductive disease, disorder or condition. In some embodiments, the subject has a cardiovascular disease, disorder or condition. In some embodiments, the subject has a gastrointestinal disease, disorder or condition. In some embodiments, the subject has a pulmonary disease, disorder or condition (e.g., pulmonary hypertension). In some embodiments, the subject has a musculoskeletal disease, disorder or condition. In some embodiments, the subject has a neurological disease, disorder or condition. In some embodiments, the subject has a reproductive disease, disorder or condition (e.g., erectile dysfunction). In some embodiments, the subject has a cancer. In some embodiments, the subject has osteoporosis or a bone fracture. In some embodiments, the subject has an inflammatory or autoimmune disease, disorder or condition. In some embodiments, the subject is in need of lowering cholesterol or lowering lipids (e.g., has high cholesterol).

As used herein, an "effective amount" is an amount of a compound that, when administered to a subject, is sufficient to achieve a desired therapeutic effect in the subject under the conditions of administration, such as an amount sufficient to inhibit (e.g., reduce, decrease, prevent) pulmonary hypertension in a subject (e.g., patient) with pulmonary hypertension. The effectiveness of a therapy (e.g., the reduction and/or prevention of pulmonary hypertension) can be determined by any suitable method known to those of skill in the art.

An effective amount of the compound to be administered can be determined by a clinician of ordinary skill using the guidance provided herein and other methods known in the art, and is dependent on several factors including, for example, the particular compound chosen, the subject's age, sensitivity, tolerance to drugs and overall well-being. For example, suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Determining the dosage for a particular agent, subject and disease is well within the abilities of one of skill in the art. Preferably, the dosage does not cause or produces minimal adverse side effects (e.g., immunogenic response, nausea, dizziness, gastric upset, hyperviscosity syndromes, congestive heart failure, stroke, pulmonary edema).

A compound described herein (e.g., a compound of any of Structural Formulas I-III, or a pharmaceutically acceptable salt of any of the foregoing) can be administered in a single dose or as multiple doses, for example, in an order and on a schedule suitable to achieve a desired therapeutic effect (e.g., inhibition of pulmonary hypertension). Suitable dosages and regimens of administration can be determined by a clinician of ordinary skill.

A compound described herein (e.g., a compound of any of Structural Formulas I-III, or a pharmaceutically acceptable salt of any of the foregoing) can also be administered in combination with one or more other therapies or treatments. With respect to the administration of a compound in combination with one or more other therapies or treatments (adjuvant, targeted, cancer treatment-associated, and the like), the agent is typically administered as a single dose (by, e.g., injection, infusion, orally), followed by repeated doses at particular intervals (e.g., one or more hours) if desired or indicated.

A compound described herein (e.g., a compound of any of Structural Formulas I-III, or a pharmaceutically acceptable salt of any of the foregoing) can be administered to the subject in need thereof as a primary therapy (e.g., as the principal therapeutic agent in a therapy or treatment regimen); as an adjunct therapy (e.g., as a therapeutic agent used together with another therapeutic agent in a therapy or treatment regime, wherein the combination of therapeutic agents provides the desired treatment; "adjunct therapy" is also referred to as "adjunctive therapy"); in combination with an adjunct therapy; as an adjuvant therapy (e.g., as a therapeutic agent that is given to the subject in need thereof after the principal therapeutic agent in a therapy or treatment regimen has been given); or in combination with an adjuvant therapy.

When administered in a combination therapy, the compound can be administered before, after or concurrently with the other therapy (e.g., an additional agent(s)). When co-administered simultaneously (e.g., concurrently), the compound and other therapy can be in separate formulations or the same formulation. Alternatively, the compound and other therapy can be administered sequentially, as separate compositions, within an appropriate time frame as determined by a skilled clinician (e.g., a time sufficient to allow an overlap of the pharmaceutical effects of the therapies).

A compound described herein (e.g., a compound of any of Structural Formulas I-III, or a pharmaceutically acceptable salt of any of the foregoing) can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound and the particular disease to be treated. Administration can be local or systemic as indicated. The preferred mode of administration can vary depending on the particular compound chosen.

The actual dose of a therapeutic agent and treatment regimen can be determined by the physician, taking into account the nature of the disease, other therapies being given, and subject characteristics.

The compounds described herein are thought to be competitive inhibitors of PDE5. Accordingly, also provided herein is a method of modulating (e.g., inhibiting, such as by competitive inhibition) PDE5 in a cell. The method comprises administering to the cell a compound described herein (e.g., a compound of any of Structural Formulas I-III, or a pharmaceutically acceptable salt of any of the foregoing). The cell can be a cultured cell (e.g., cell line) or a cell in a subject. In a particular embodiment, the cell is present in a human subject (e.g., a human subject with a PDE5-mediated disease).

EXEMPLIFICATION

In this study, the structure-function relationship of six icariin analogs (3-8), together with three previously described and naturally occurring icariin analogs (1, 2, and 9) was characterized in the context of human PDE5 inhibition. The substituents at the 7-O and the 3-O positions of the icariin backbone may exert a synergistic impact on PDE5 inhibition potency although hydrophobic interactions may be the main driver of icariin-based PDE5 inhibition. Compounds 3 and 7 are the most potent of the icariin analogs described herein, with an $IC_{50}$ and $K_i$ similar to other synthetic PDE5 inhibitors.

Design and Synthesis of Icariin Analogs

A crystal structure of the human PDE5 catalytic domain complexed to icariside II (1) shows that the 3-O-rhamnose is buried deep within the active site, forming a hydrogen bond with Asp764, which is predicted to play a role in catalysis. The 7-OH of icariside II (1) is located near the active site entrance and forms a hydrogen bond with Ser668 on the flexible H-loop (residues 660-683 of human PDE5A1 in the complex assigned Protein Data Bank Accession No.: 2H44). Crystal structures show that the H-loop adopts significantly different secondary structure and proximity to the active site entrance when PDE5 binds to different inhibitors, even if the inhibitors share the same structural backbone (for example, sildenafil and vardenafil).

A series of nine icariin analogs was synthesized according to Scheme 1. Analogs with either the 7-O-glucose or the 3-O-rhamnose replaced with a free hydroxyl (1 and 2, respectively) were synthesized to evaluate the contribution of each sugar group to PDE5 inhibition. The aglycone of icariin (9) was synthesized to determine the contribution of the core structure to PDE5 inhibition. Then, the 3-OH of 2 was modified with either a hydroxyethyl, a hydroxypropyl, or a hydroxyisopropyl group (3, 4, and 5, respectively). To evaluate the 3-O-alkanol contributions to PDE5 inhibition, the 7-O-glucose in 3-5 was replaced with a free hydroxyl to afford 6-8.

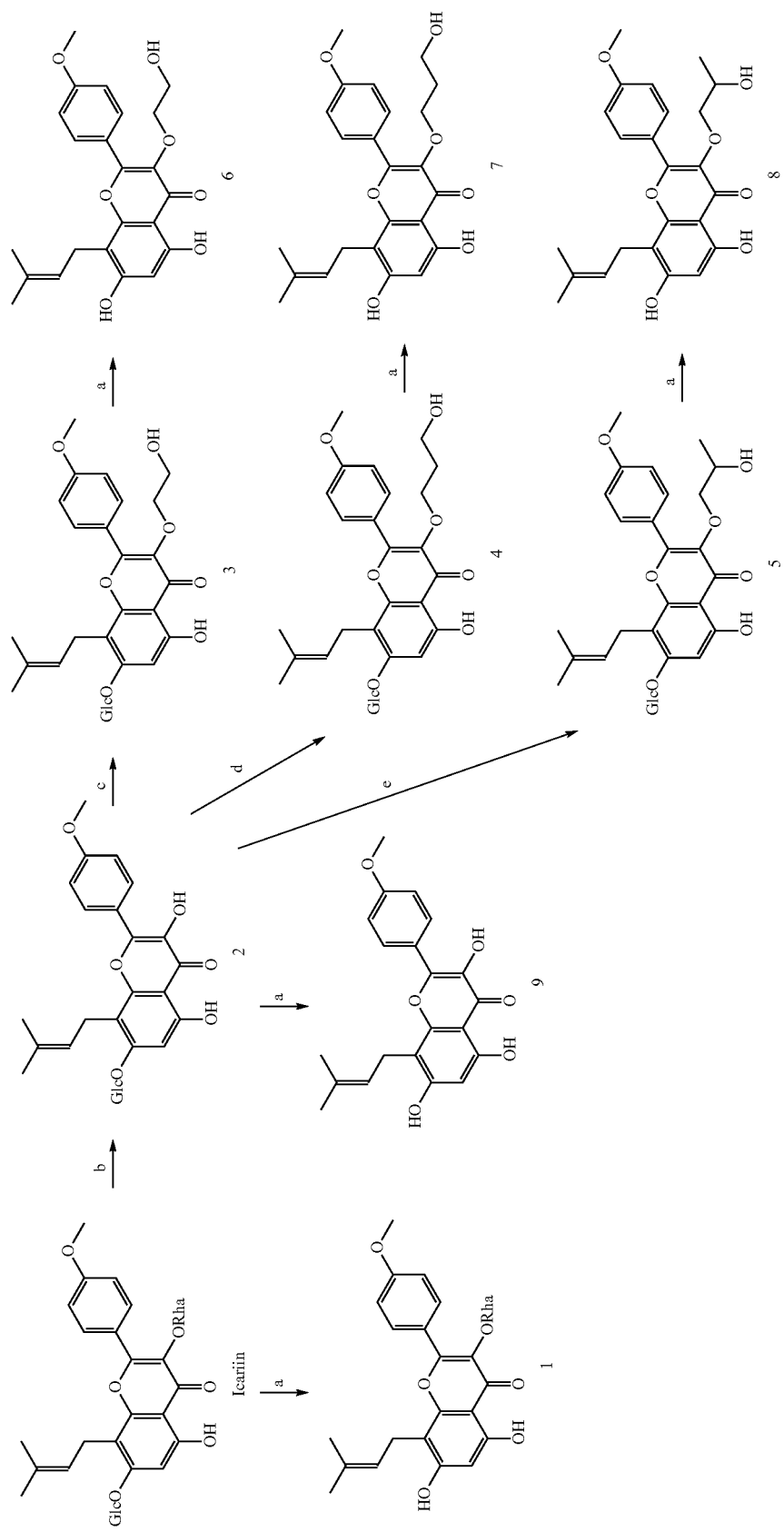
Scheme 1. Structures of Icariin Analogs 1-9 and their synthetic routes.
(a) cellulase, 0.1M NaOAc, pH = 5.7, 37° C., overnight. (b) 5% $H_2SO_4$, 50° C., 24 hours. (c) 2-bromoethanol, $K_2CO_3$, refluxed, 8 hours. (d) 3-Bromo-1-propanol, $K_2CO_3$, refluxed, 8 hours. (e) 1-bromo-2-propanol, $K_2CO_3$, 75° C., 6 hours. Glc = glucose, Rha = rhamnose.

Select Icariin Analogs Exhibit Enhanced Inhibition Potencies

To evaluate the nine icariin analogs, the $IC_{50}$ of each analog, icariin, and sildenafil were measured in an in vitro PDE5 inhibition assay, which measures GMP production from cGMP by purified recombinant human PDE5. Table 1 summarizes the $IC_{50}$ values obtained for the nine icariin analogs tested. Fold improved potency in Table 1 refers to fold change in $IC_{50}$ compared to icariin.

TABLE 1

Summary of $IC_{50}$ Values Obtained For Icariin Analogs.

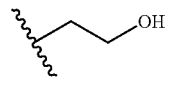 [SMILES: *CCO]

| | R | R' | IC50, µM | Field improved potency |
|---|---|---|---|---|
| icariin | Glc | Rha | 6 ± 1 | 1 |
| 1 | H | Rha | 8.8 ± 1.0 | 0.7 |
| 2 | Glc | H | 2.1 ± 0.8 | 3 |
| 3 | Glc | 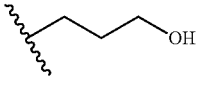 [SMILES: *CCCO] | 0.083 ± 0.010 | 72 |
| 4 | Glc | 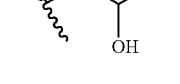 | 0.8 ± 0.5 | 8 |
| 5 | Glc | 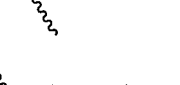 | 0.5 ± 0.1 | 12 |
| 6 | H | 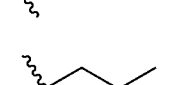 | 0.4 ± 0.2 | 15 |
| 7 | H | 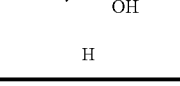 | 0.14 ± 0.06 | 43 |
| 8 | H | 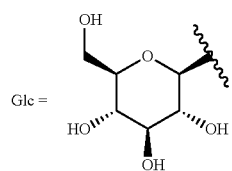 [SMILES: *[C@@H]1O[C@H](CO)[C@@H](O)[C@H](O)[C@H]1O] | 1.5 ± 0.6 | 4 |
| 9 | H | H | 1.8 ± 0.8 | 3 |

Glc = 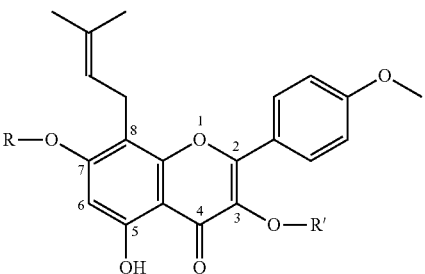

Rha = 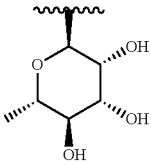

The $IC_{50}$ values obtained for sildenafil and icariin agree with previous reports (0.028±0.007 µM and 6±1 µM, respectively). Replacing only the 7-O-glucose with a free hydroxyl (1) leads to a slight loss in potency (IC50 8.8±1.0 µM). This finding conflicts with the study by Dell'Agli et al. that reported that 1 has an $IC_{50}$ of 0.16 µM and a 34-fold improvement in PDE5 inhibition compared to icariin. This could be due to differences in assay design, such as enzyme purity, since highly purified human PDE5 was used here, whereas Dell'Agli et al. used the lysate of COS-7 cells expressing human PDE5 in their enzyme activity assays. Replacing only the 3-O-rhamnose with a free hydroxyl (2) or replacing both sugars with a free hydroxyl (9) leads to an approximately 3-fold improvement in potency compared to icariin (IC50 2.1±0.8 and 1.8±0.8 µM respectively). The IC50 value obtained for 9 (also referred to as icaritin) agrees with the value reported by Dell'agli et al. These results support the thesis that removing the bulky rhamnose located deep within the active site leads to improved PDE5 inhibition and that retaining the glucose group does not seem to negatively impact PDE5 inhibition.

Compounds 6-8 were used to evaluate the effects of alkylating the 3-OH with a hydroxyethyl (6), a hydroxypropyl (7), or a hydroxyisopropyl (8) group on PDE5 inhibition in the absence of the 7-O-glucose. Compound 8 (IC50 1.5±0.6 µM) shows a 4-fold improvement over icariin, and compound 6 (IC50 0.4±0.2 µM) shows a 15-fold improvement. Compound 7 (IC50 0.14±0.06 µM) shows a 42-fold improvement in inhibition, and the $IC_{50}$ approaches those of other synthetic PDE5 inhibitors. These results suggest that installation of a linear alkanol group, particularly a hydroxypropyl group, at the 3-OH is sufficient to significantly enhance PDE5 inhibition by an icariin analog.

Combining the 7-O-glucose with a 3-O-alkanol leads to improved PDE5 inhibition compared to analogs with only the 3-O-alkanol when the 3-OH is alkylated with either a hydroxyethyl group (3; IC50 0.083±0.010 µM) or a hydroxyisopropyl group (5; IC50 0.5±0.1 µM). A 5- and 3-fold increase in potency compared to the unglycosylated analogs 6 and 8 were observed for 3 and 5, respectively. Compound 3 was the most potent icariin analog with an $IC_{50}$ of 0.083±0.010 µM, representing a 72-fold increase in potency compared to icariin and approaching the inhibitory potencies of other synthetic PDE5 inhibitors. Compound 5 shows a 12-fold improvement in potency. This supports the thesis that combining the 7-O-glucose with a 3-O-alkanol improves PDE5 inhibition. These observations are in contrast with the results for 4 (IC50 0.8±0.5 µM). In this case, combining the 7-O-glucose with the 3-O-hydroxypropyl group leads to a decrease in potency by 6-fold compared to the unglycosylated 7 and only an 8-fold improvement in potency compared to icariin. In summary, the two most potent icariin analogs synthesized were 3 and 7, which exhibit 72- and 43-fold improvement in PDE5 inhibition, respectively, compared to icariin.

Compound 3 combines both a 7-O-glucose and a 3-O-hydroxyethyl group. Compound 3 is more potent than 6, which only has a 3-O-hydroxyethyl, and 2, which only has a 7-O-glucose. Combining the 7-O-glucose with a 3-O-alkanol enhances (3 and 5) or reduces (4) the PDE5 inhibition potency of icariin analogs. These results suggest that the 3-O and 7-O functional groups act synergistically. It is possible that binding of icariin analogs with shorter functional groups at C3, such as a 3-O-hydroxyethyl and a 3-O-hydroxyisopropyl group in compounds 3, 5, 6 and 8, may be aided by interactions between the protein and the 7-O-glucose. Even though the hydroxypropyl group in 4 is only one carbon longer than the hydroxyethyl group in 3, it is possible that a slightly shorter functional group at the C3 position allows a better "fit" of the 7-O-glucose in the active site. Since the PDE5 H-loop is reported to adopt alternative conformations when different inhibitors bind to PDE5, it is also possible that the shorter C3 groups and a 7-O-glucose (and, in particular, the combination presented by 3) induces a specific conformation within the PDE5 H-loop that promotes PDE5 inhibition.

On the whole, these results suggest that a hydrophobic group at the 3-0 position contributes significantly to PDE5 inhibition by icariin analogs.

Enzyme Kinetics Reveal $K_i$ and Competitive Inhibition Models for Compounds 3 and 7

Figure 1B:
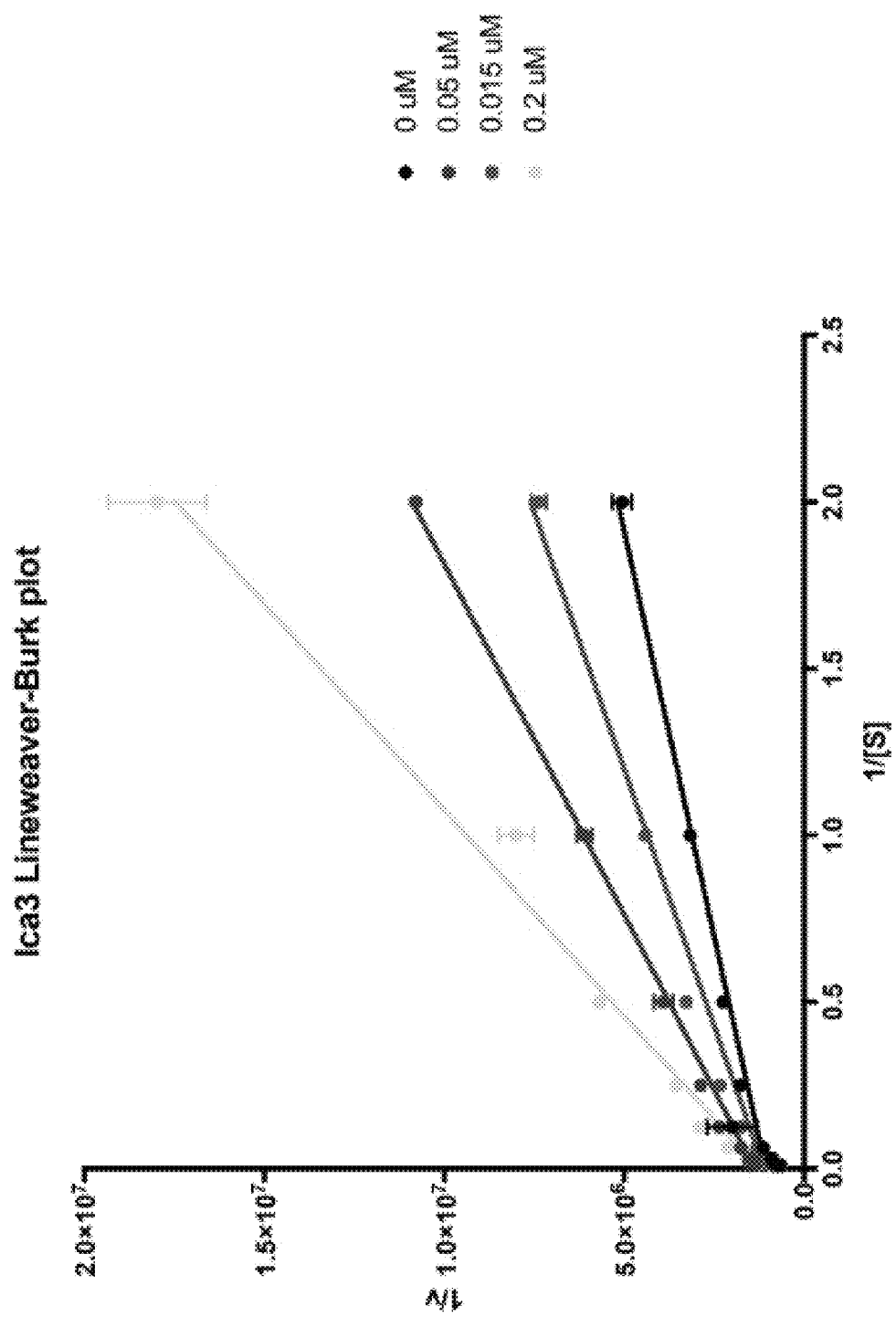
FIG. 1B is a Lineweaver-Burk plot of the enzyme kinetic curve of FIG. 1A.
Figure 1C:
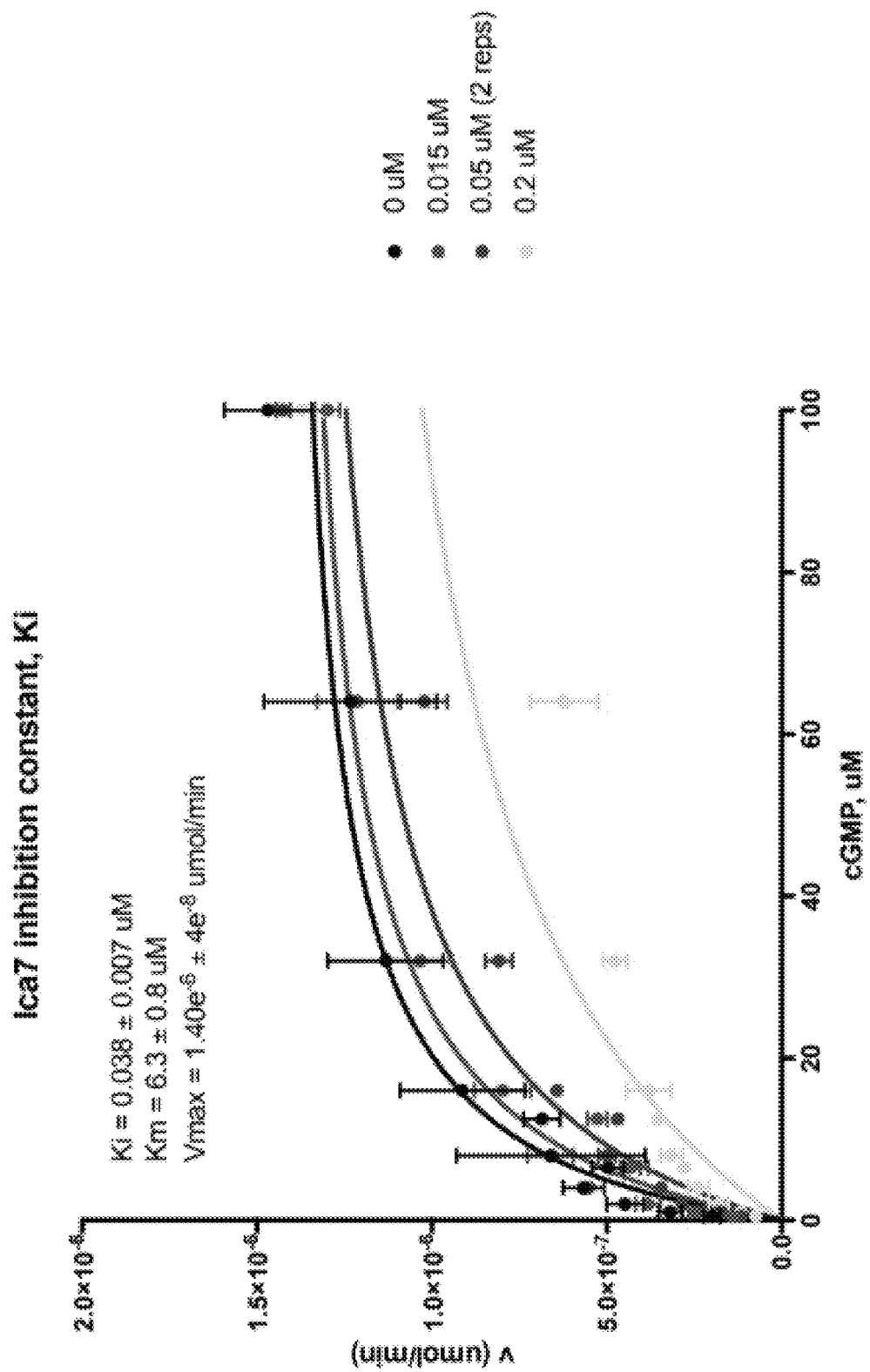
FIG. 1C is an enzyme kinetic curve obtained with Ica7.
Figure 1D:
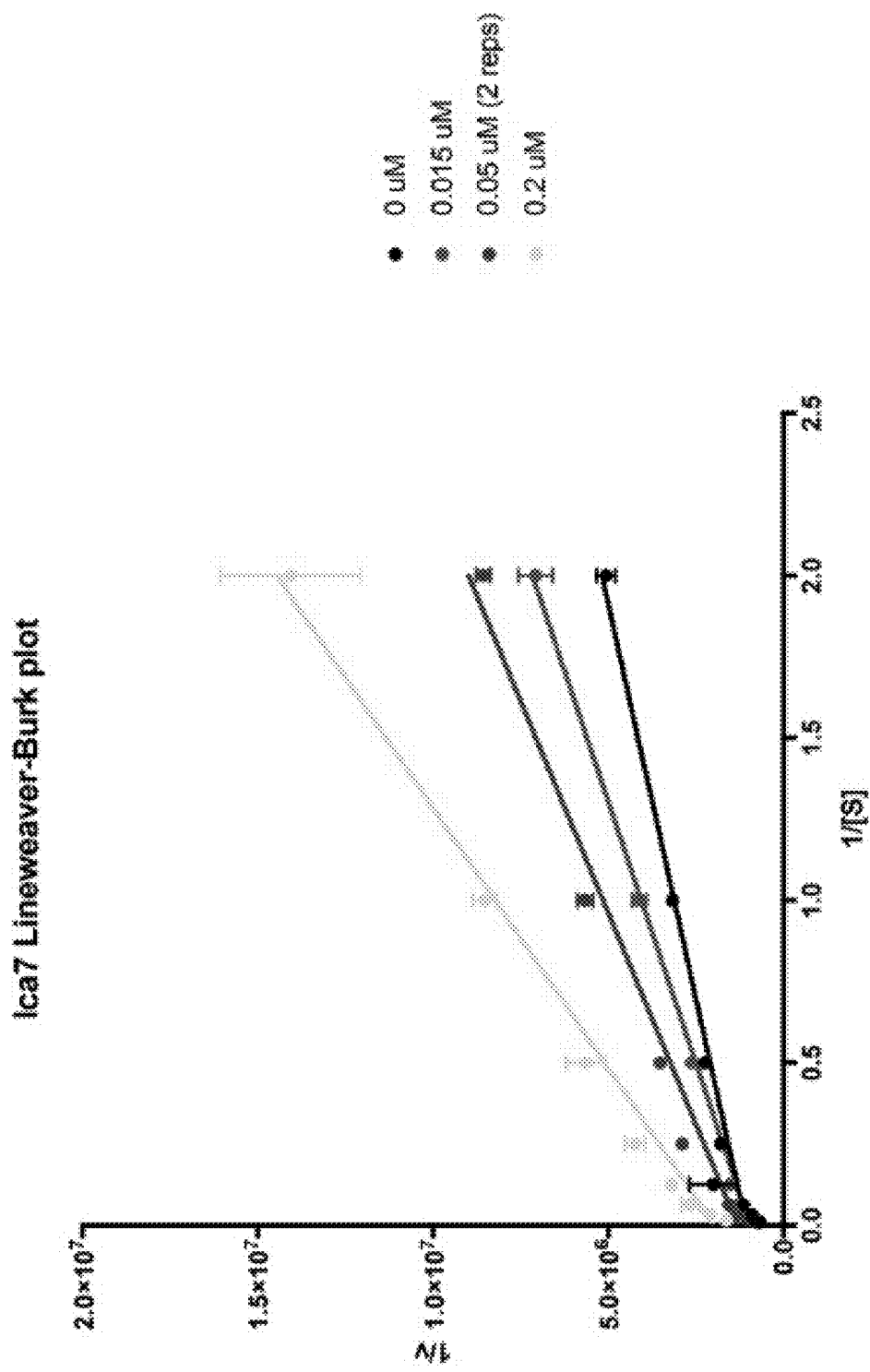
FIG. 1D is a Lineweaver-Burk plot of the enzyme kinetic curve of FIG. 1B.

A crystal structure of PDE5 bound to icariside II (1) showing icariside II binding to the active site like a competitive inhibitor has been published and $IC_{50}$ values have been reported for several icariin analogs. While the icariin analogs disclosed herein share the core structure of icariside II, modifying the C3 and C7 positions may change its mode of inhibition. The $K_i$ of 3 and 7 was determined using the in vitro PDE5 inhibition assay and purified recombinant human PDE5 previously described. FIG. 1A shows that 3 has a $K_1$ of 0.036±0.005 µM, and FIG. 1C shows that 7 has a $K_i$ of 0.038±0.007 µM. FIGS. 1B and 1D are the Lineweaver-Burk plots of the curves plotted in FIGS. 1A and 1C, respectively. Both compounds show characteristics of competitive inhibitors. The $K_m$ for PDE5 has a value of 6.3-6.5±0.8 µM, which is consistent with previously published reports.

Molecular Modeling Reveals Features Dictating Icariin Analog Binding to PDE5

Figure 2A:
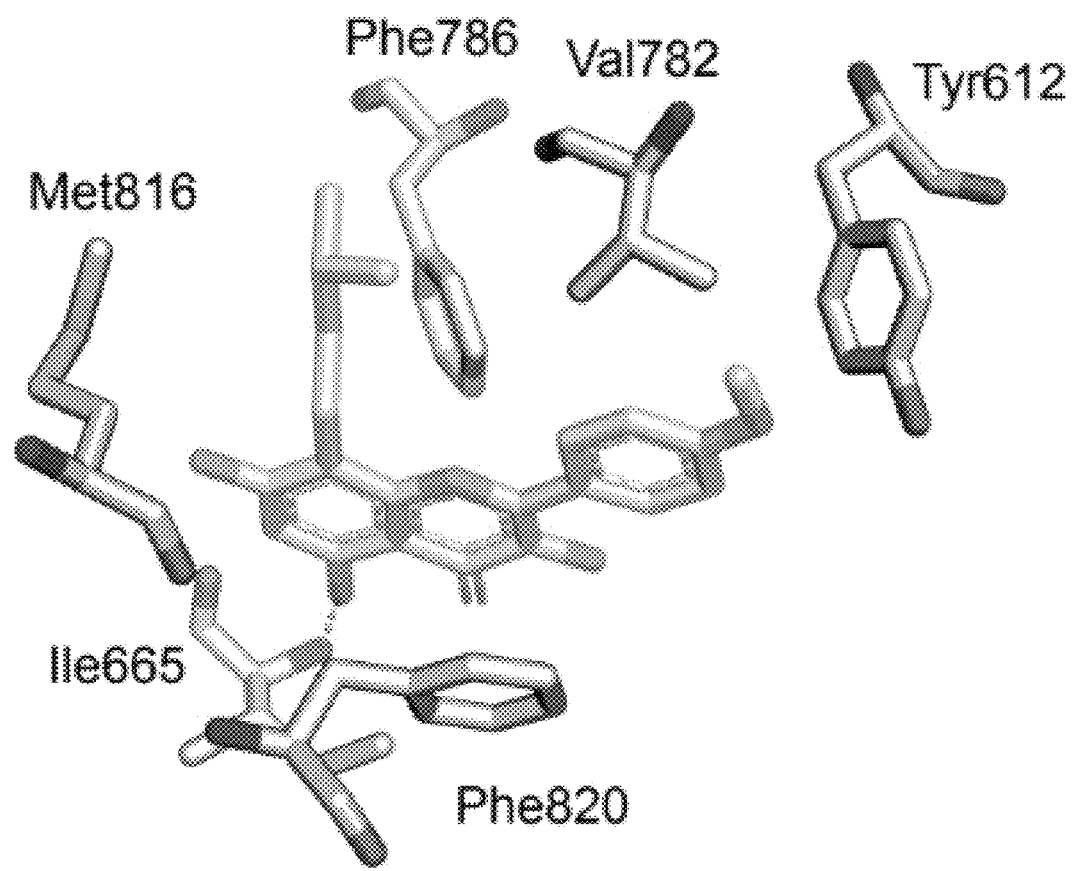
FIG. 2A shows the results of molecular modeling of human PDE5 with the icariin aglycone. The icariin aglycone is shown in pink, PDE5 residues interacting with the icariin aglycone are shown in white.

In order to rationalize the observed structure-function relationships between the icariin analogs and PDE5, a set of ligand-docking simulations was conducted using the pre-existing co-crystal structure of PDE5 bound to icariside II (1). All the icariin analogs tested shared an identical core structure (the icariin aglycone, 9), and consequently, there is a set of conserved interactions between the PDE5 residues and the various analogs. FIG. 2A shows the conserved interactions with the icariin core structure. For instance, a group of aromatic residues—Tyr612, Phe786, and Phe820—are involved in aromatic π-π interactions. Furthermore, the conserved prenyl group is bound in a hydrophobic pocket composed of Val782, Phe786, and Met816, and the conserved 5-OH is hydrogen bonding with the backbone amine of Ile665.

Figure 2B:
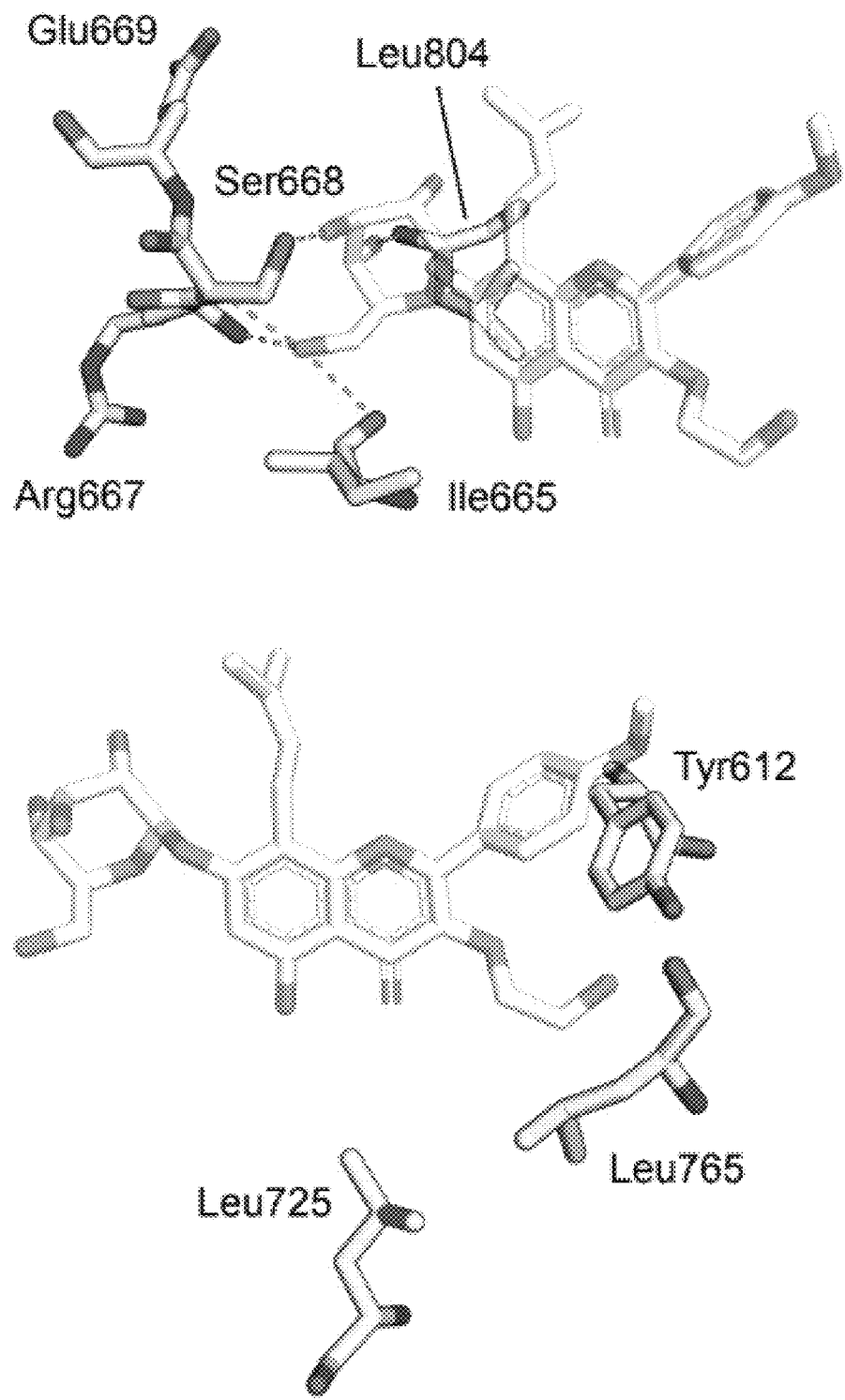
FIG. 2B shows the results of molecular modeling of human PDE5 with Ica3. Ica3 is shown in white, PDE5 residues interacting with the 7-O-substituent are shown in blue and PDE5 residues interacting with the 3-O-substituent are shown in yellow.
Figure 2C:
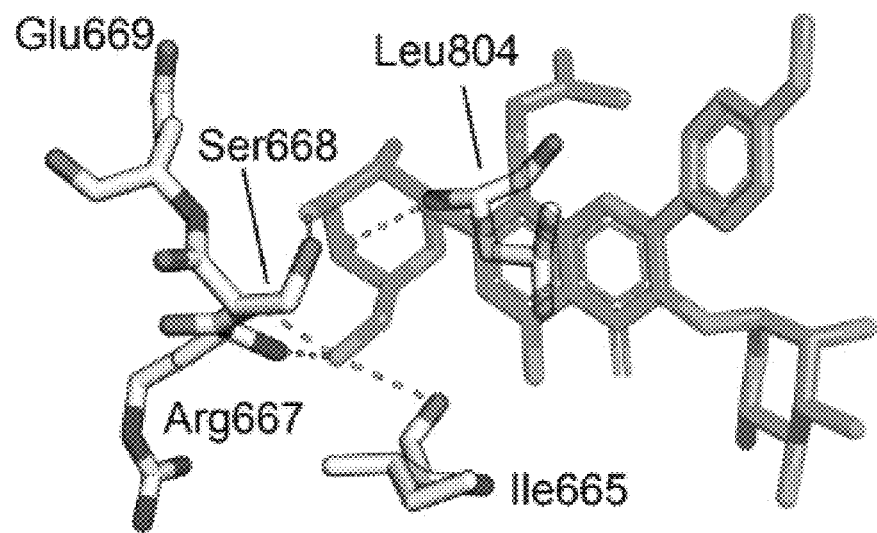
FIG. 2C shows the results of molecular modeling of human PDE5 with icariin. Icariin is shown in black, PDE5 residues interacting with the 7-O-substituent are shown in blue and PDE5 residues interacting with the 3-O-substituent are shown in yellow.
Figure 2C:
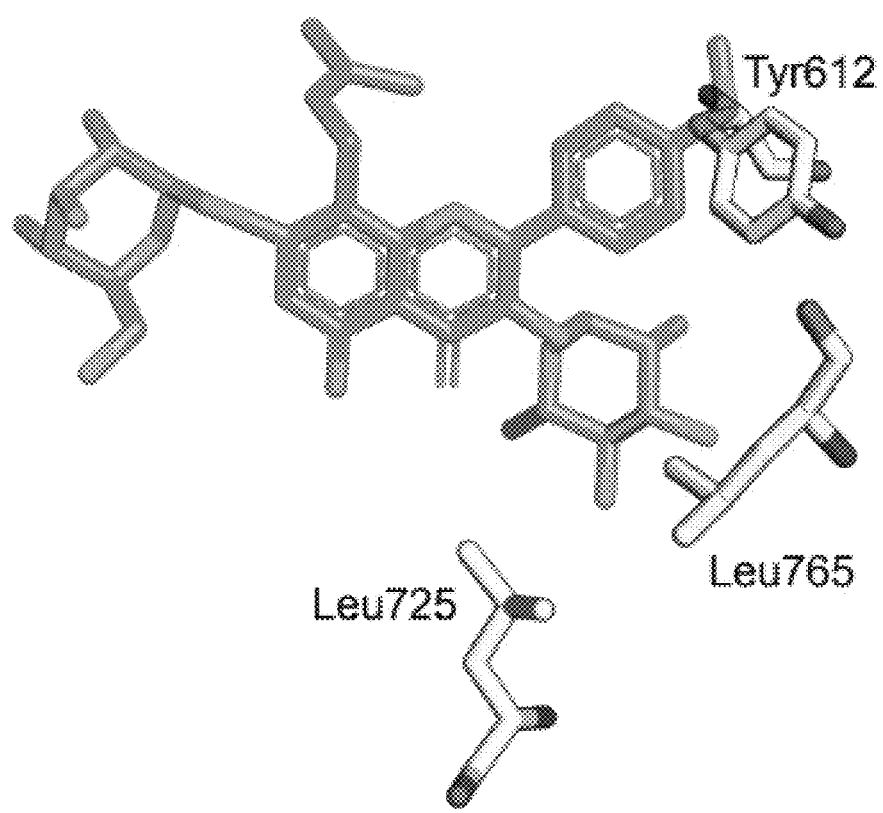

Next, the class of analogs containing the 7-O-glucose was modeled. FIGS. 2B and 2C (top) show that a number of PDE5 residues interact with the 7-O-glucose. These include Ile665, Arg 667, Ser668, Glu669, and Leu804, which contribute one or more stabilizing hydrogen bonds. Many of these residues are located in the H-loop, which is known to reflect the ligand binding affinity based on its variable secondary structure and location. Although the molecular modeling method used is unable to capture long-range conformational shifts, its structural identity is likely to be represented with fidelity due to the starting model, which was based on a crystal structure of PDE5 bound to icariside II (1).

The contribution of the 3-O-rhamnose in icariside II (1) and icariin to PDE5 binding was also modeled. A set of hydrophobic residues consisting of Tyr612, Leu725, and Leu765 surrounds the rhamnose binding site and creates a hydrophobic pocket. FIGS. 2B and 2C (bottom) show the hydrophobic interactions with 3-O-alkanols. As a result, the rhamnose only forms two hydrogen bonds with the surrounding residues His613 and Asp764, a contribution which may be offset by the presence of a hydrophilic carbohydrate in a hydrophobic binding area. This observation explains the binding preference of analogs with 3-O-alkanols (2-8) over those with 3-O-rhamnose (2). Furthermore, considering that 6 and 7 have low $IC_{50}$ values, this suggests that the contribution of 3-O-alkanols outweighs that of the 7-O-glucose with regard to binding affinity. Following this logic, the higher $IC_{50}$ value of 9 can be explained by its lack of functional groups at both the C3 and C7 positions, resulting in a loss of stabilizing interactions with PDE5. However, the results do not discern why there is a preference for linear alkanol modification at 3-OH over those that are branched, suggesting that there may be additional conformational changes that account for this not captured in this model.

Icariin Analogs are Generally not Toxic to Human Cells

Figure 3A:
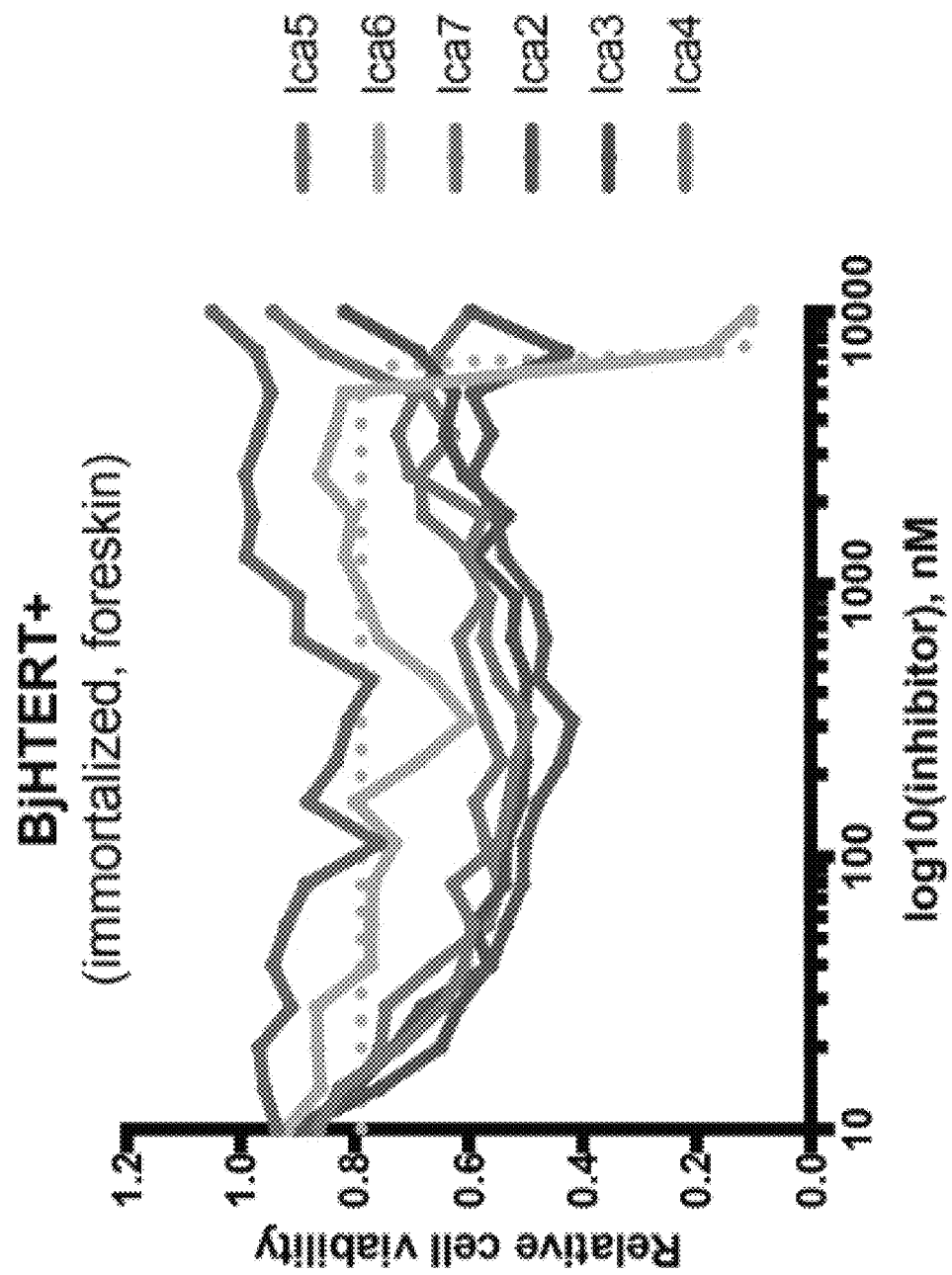
FIG. 3A shows cytotoxicity data measured by resazurin against BJHTERT+ cells treated with 0-10 μM Ica2, Ica3, Ica4, Ica5, Ica6 or Ica7.
Figure 3B:
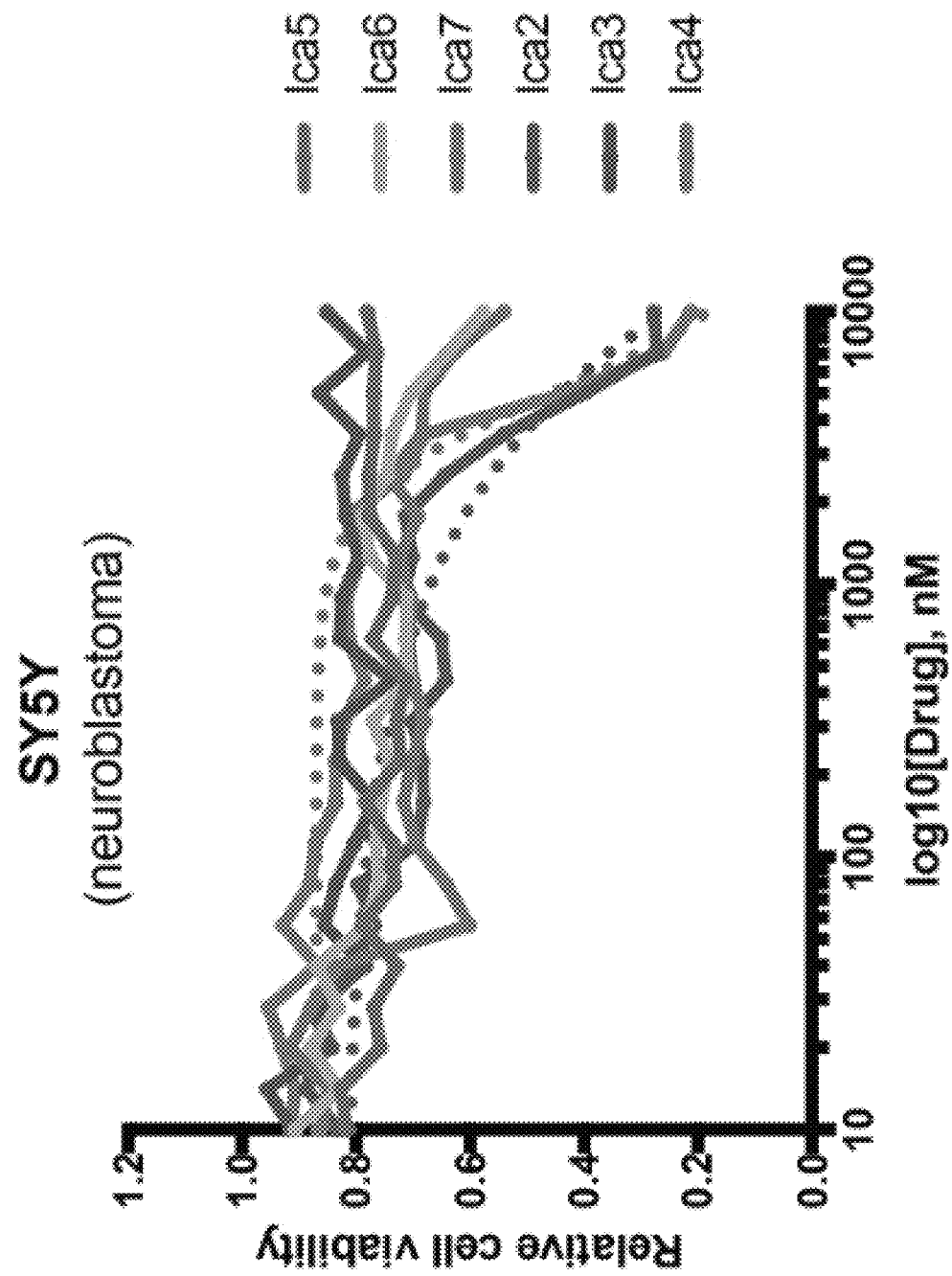
FIG. 3B shows cytotoxicity data measured by resazurin against SY5Y cells treated with 0-10 μM Ica2, Ica3, Ica4, Ica5, Ica6 or Ica7.
Figure 3C:
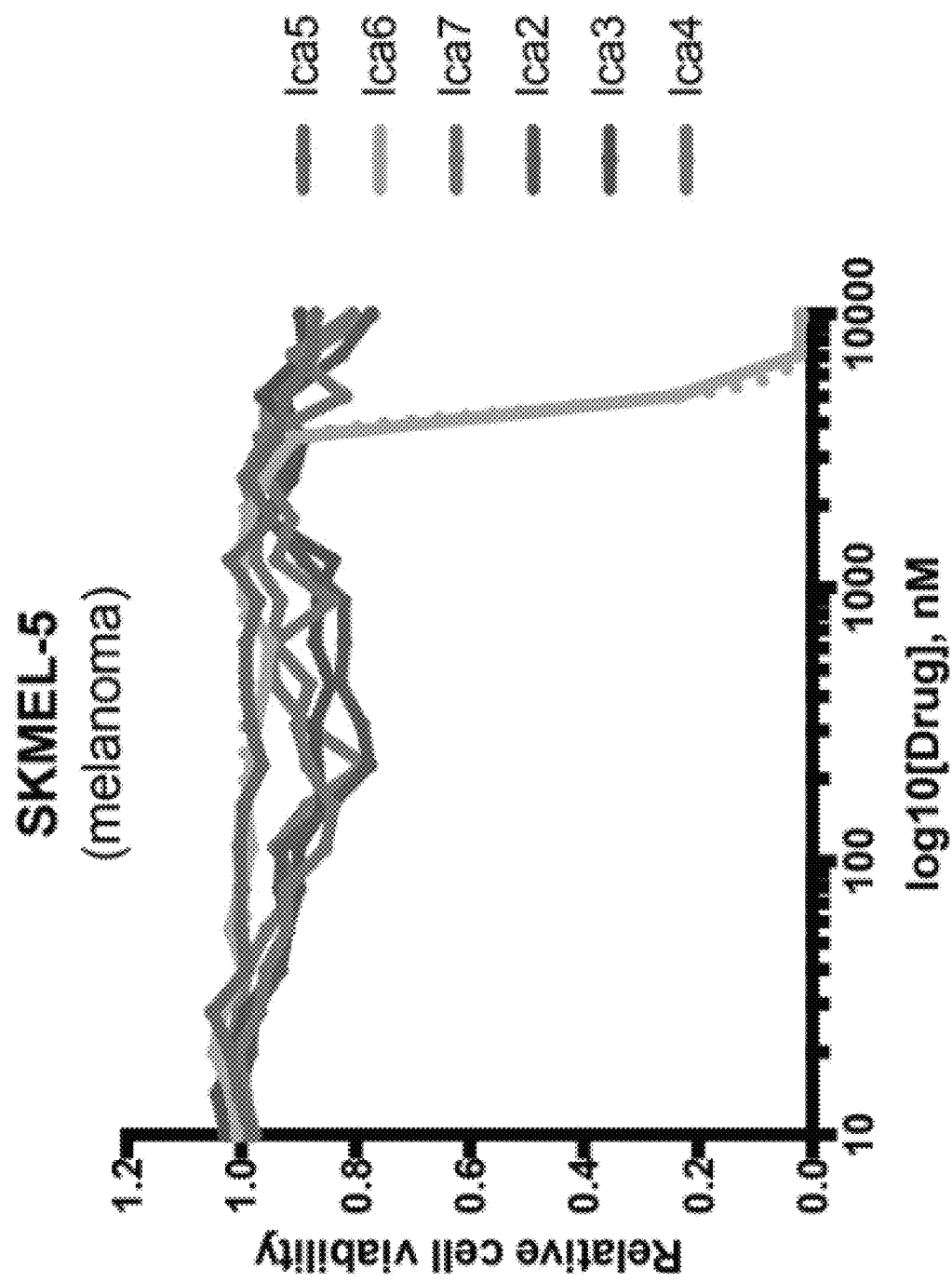
FIG. 3C shows cytotoxicity data measured by resazurin against SKMEL-5 cells treated with 0-10 μM Ica2, Ica3, Ica4, Ica5, Ica6 or Ica7.
Figure 3D:
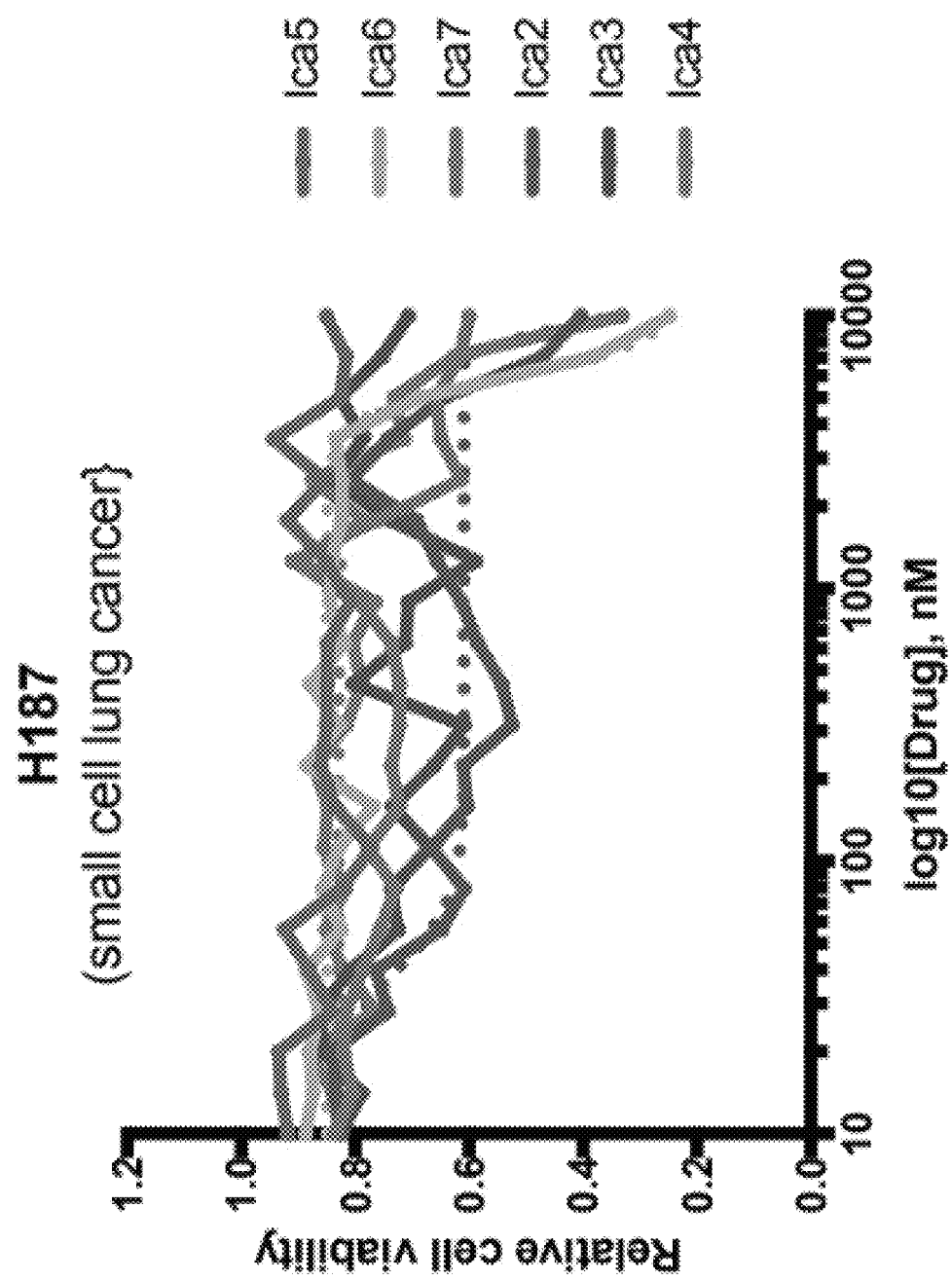
FIG. 3D shows cytotoxicity data measured by resazurin against H187 cells treated with 0-10 μM Ica2, Ica3, Ica4, Ica5, Ica6 or Ica7.
Figure 3E:
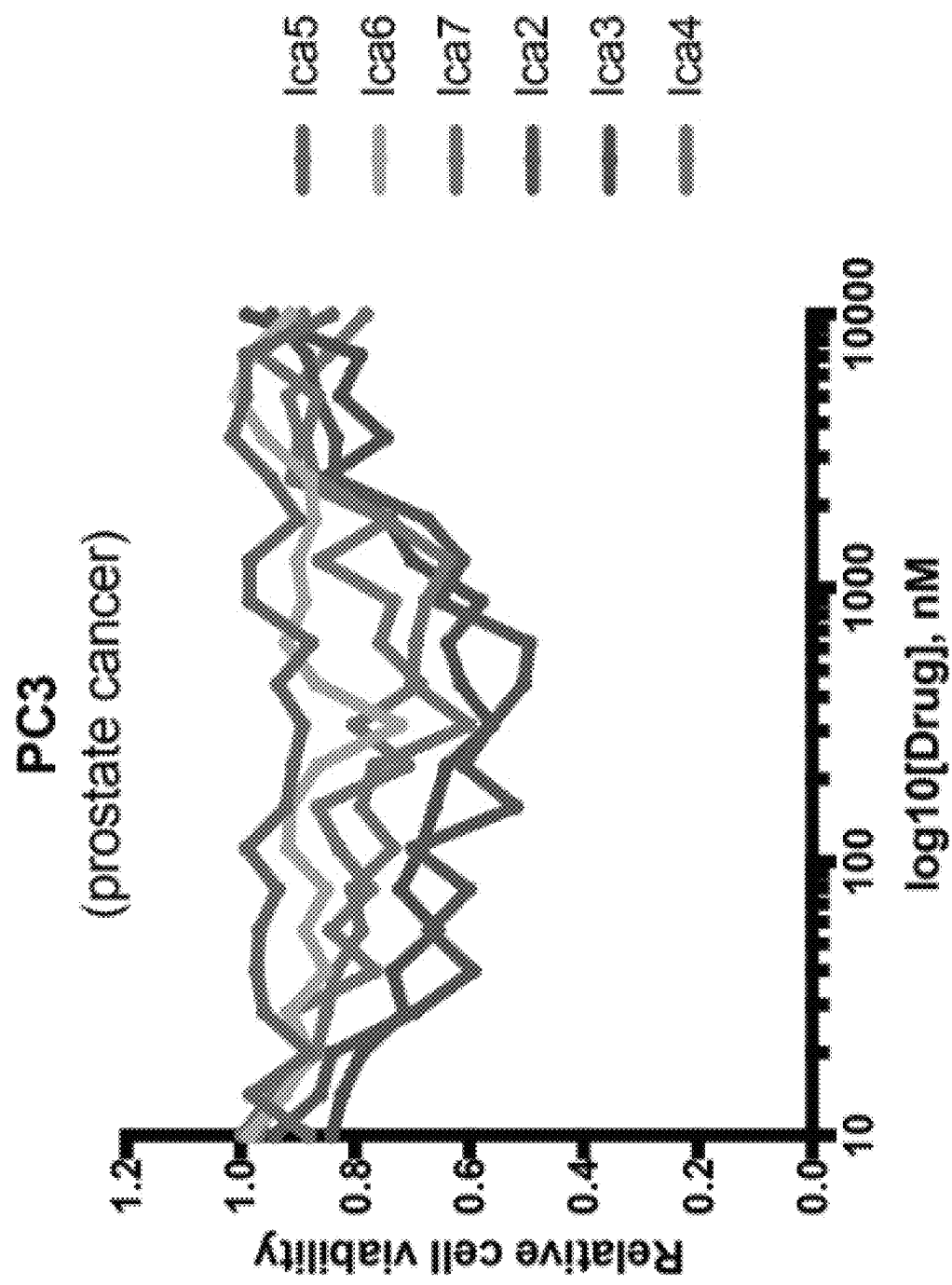
FIG. 3E shows cytotoxicity data measured by resazurin against PC3 cells treated with 0-10 μM Ica2, Ica3, Ica4, Ica5, Ica6 or Ica7.

A general feature of compounds with promise as viable therapeutics is a lack of toxicity to human cells. To test the icariin analogs for this feature, each analog was assayed against a panel of five human cell lines for cytotoxicity. The five human cell lines represent various tissue types—normalized, untransformed epithelial cells derived from fetal foreskin, neuroblastoma, melanoma, prostate, and lung. A Western blot against PDE5 confirmed that all five cell lines express PDE5 protein (data not shown). Compounds 2-7 were assayed at concentrations ranging from 0-10 µM, ensuring that all compounds remained soluble. All icariin analogs except 2, 4, and 6 did not cause defects in growth or proliferation based on measurements with resazurin. See FIGS. 3A-3E. Compounds 2 and 4 caused toxicity to two out of the five cell lines assayed with an $IC_{50}$>10 µM. See FIGS. 3B and 3D. Compound 6 caused toxicity in three out of the five cell lines assayed with an $IC_{50}$ of 4-7 µM. See FIGS. 3A, 3C and 3D. The $IC_{50}$ values of 2, 4 and 6 in the tested human cell lines in which they exhibited toxicity is reported in Table 2.

TABLE 2

IC$_{50}$ Values (µM) of 2, 4 and 6 in SY5Y, SKMEL-5, BjH+ and H187 Cell Lines.

|  | Ica6 | Ica2 | Ica4 |
|---|---|---|---|
| SY5Y |  | >10 | 5.02 |
| SKMEL-5 | 4.45 |  |  |
| BjH+ | 6.73 |  |  |
| H187 | 5.92 | >10 | >10 |

Materials and Methods

Reagents. All chemicals were purchased from Sigma-Aldrich, unless otherwise specified. Solvents for liquid chromatography high-resolution mass spectrometry were Optima® LC-MS grade (Fisher Scientific) or LiChrosolv® LC-MS grade (Millipore). Low-resolution mass spectrometry analysis was done on a Thermo ESI-QQQ MS coupled to a Thermo Ultimate 3000 UHPLC system. Solution NMR spectra were recorded on a Bruker AVANCE-400 NMR spectrometer with a Spectro Spin superconducting magnet in the Massachusetts Institute of Technology, Department of Chemistry Instrumentation Facility (MIT DCIF). The purity of final compounds was analyzed by HPLC-UV-MS with the purity of all compounds being over than 95%. The HPLC instruments equipped with Thermo ESI-QQQ MS coupled to a Thermo Ultimate 3000 UHPLC system, using Phenomenex Kinetex® 2.6 µm C$_{18}$ reverse phase 100 Å 150×3 mm LC column, the mobile phases were: solvent A-water (0.1% formic acid), solvent B-acetonitrile (0.1% formic acid), 0-4 minutes 0% B, 4-7 minutes 0-95% B, 7-9 minutes 95% B, 9-11 minutes 0% B, 0.5 ml/min).

Synthesis of Icariin Analogs 1-9.

Compound 1 (Ica1) was synthesized according to a modified method of Dell'Agli et al. A solution of icariin (100 mg) in DMSO (1 mL) was added to a 0.1 M Na acetate buffer (pH 5.7, 50 mL) at 37° C. containing cellulase (60 mg). The suspension obtained was stirred at 37° C. overnight. Then the mixture was extracted with EtOAc (3×200 mL). The organic layer was dried over anhydrous Na$_2$SO$_4$ and evaporated under reduced pressure. The residue was purified by column chromatography on LH20 (MeOH) to afford 1 (60 mg). $^1$H NMR (DMSO-d$_6$, 400 MHz), δ 12.52 (1H, s, OH-5), 7.84 (2H, d, J=8.8 Hz, H-2', 6'), 7.11 (2H, d, J=8.8 Hz, H-3', 5'), 6.31 (1H, s, H-6), 5.15 (1H, t, J=6.4 Hz, H-12), 4.63-5.26 (3H, m, Rha-OH), 3.05-4.64 (5H, m, Rha-H), 3.85 (3H, s, OCH$_3$), 3.43 (2H, d, J=6.8 Hz, H-11), 1.70, 1.62 (3H, 3H, s, CH$_3$-14, 15), 0.77 (3H, d, J=6.0 Hz, Rha-CH$_3$). ESIMS (positive-ion mode) m/z 515 [M+H]$^+$. HPLC purity: 97.23%, retention time=10.48 min.

Compound 2 (Ica2) was synthesized according to a method of Shen. A solution of icariin (800 mg) in ethanol (11 mL) was added to 11 mL 5% aqueous sulfuric acid solution, stirred for 24 hours at 50° C., cooled to room temperature, and concentrated under reduced pressure to remove ethanol. Then, the mixture was extracted with EtOAc (3×200 mL) and washed with saturated brine and NaHCO$_3$ solution (2×200 mL). The organic layer was dried over anhydrous Na$_2$SO$_4$ and evaporated under reduced pressure. The residue was purified by column chromatography on LH20 (MeOH) to afford 2 (450 mg). $^1$H NMR (DMSO-d$_6$, 400 MHz), δ 12.43 (1H, s, OH-5), 9.61 (1H, s, OH-3), 8.14 (2H, d, J=8.8 Hz, H-2', 6'), 7.13 (2H, d, J=8.8 Hz, H-3', 5'), 6.60 (1H, s, H-6), 5.21 (1H, t, J=6.8 Hz, H-12), 4.63-5.34 (4H, m, Glu-OH), 5.00 (1H, d, J=6.8 Hz, Glu-H), 3.14-3.76 (6H, m, Glu-H), 3.85 (3H, s, OCH$_3$), 3.43 (2H, d, J=6.8 Hz, H-11), 1.77, 1.62 (3H, 3H, s, CH$_3$-14, 15). ESIMS (positive-ion mode) m/z 531 [M+H]$^+$. HPLC purity: 96.59%, retention time=9.92 min.

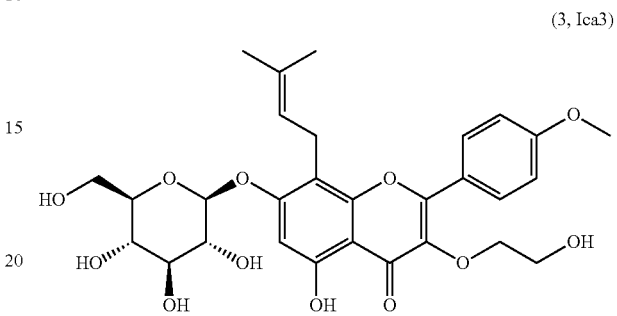

(3, Ica3)

Compound 3 (Ica3) was synthesized according to a modified method of Dell'Agli et al. A stirred suspension of 2 (50 mg), 2-bromoethanol (0.15 mL), and anhydrous K$_2$CO$_3$ (150 mg) in dry acetone (35 mL) was refluxed for 8 hours. After the reaction mixture cooled, the solvent was evaporated under reduced pressure, and the residue was suspended in 200 mL H$_2$O and extracted with EtOAc (3×200 mL). The organic layer was dried over anhydrous Na$_2$SO$_4$ and evaporated under reduced pressure. The residue was purified by column chromatography on LH20 (MeOH) to afford 3 (10 mg). $^1$H NMR (DMSO-d$_6$, 400 MHz), δ 12.63 (1H, s, OH-5), 8.17 (2H, d, J=8.8 Hz, H-2', 6'), 7.12 (2H, d, J=8.8 Hz, H-3', 5'), 6.62 (1H, s, H-6), 5.19 (1H, t, J=7.2 Hz, H-12), 4.82 (1H, t, J=4.8 Hz, OH-17), 4.62-5.34 (4H, m, Glu-OH), 5.00 (1H, d, J=6.0 Hz, Glu-H), 3.17-3.74 (6H, m, Glu-H), 4.07 (1H, t, J=4.8 Hz, H-17), 3.66 (1H, t, J=5.2 Hz, H-16), 3.87 (3H, s, OCH$_3$), 3.43 (2H, m, H-11), 1.75, 1.62 (3H, 3H, s, CH$_3$-14, 15). ESIMS (positive-ion mode) m/z 575 [M+H]$^+$. HPLC purity: 95.02%, retention time=8.99 min.

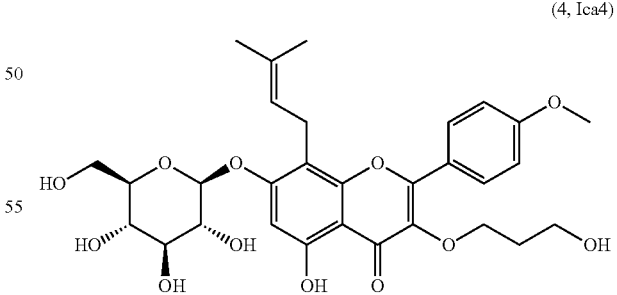

(4, Ica4)

Compound 4 (Ica4) was synthesized using a procedure similar to that used to prepare 3. A stirred suspension of 2 (150 mg), 3-bromo-1-propanol (0.15 mL), and anhydrous K$_2$CO$_3$ (230 mg) in dry acetone (35 mL) was refluxed for 8 hours. After the reaction mixture cooled, the solvent was evaporated under reduced pressure, and the residue was suspended in 200 mL H$_2$O and extracted with EtOAc (3×200 mL). The organic layer was dried over anhydrous $Na_2SO_4$, and evaporated under reduced pressure. The residue was purified by column chromatography on LH20 (MeOH) to afford 4 (80 mg). $^1$H NMR (DMSO-$d_6$, 400 MHz), δ 12.64 (1H, s, OH-5), 8.05 (2H, d, J=9.2 Hz, H-2', 6'), 7.15 (2H, d, J=9.2 Hz, H-3', 5'), 6.62 (1H, s, H-6), 5.19 (1H, t, J=6.8 Hz, H-12), 4.46-5.34 (4H, m, Glu-OH), 4.99 (1H, d, J=6.8 Hz, Glu-H), 3.17-3.74 (6H, m, Glu-H), 4.62 (1H, t, J=6.0 Hz, OH-18), 4.06 (1H, t, J=6.8 Hz, H-18), 3.49 (1H, t, J=6.0 Hz, H-16), 3.87 (3H, s, $OCH_3$), 3.43 (2H, m, H-11), 1.79 (1H, t, J=6.8 Hz, H-17), 1.73, 1.62 (3H, 3H, s, $CH_3$-14, 15). ESIMS (positive-ion mode) m/z 589 [M+H]$^+$. HPLC purity: 95.45%, retention time=9.65 min.

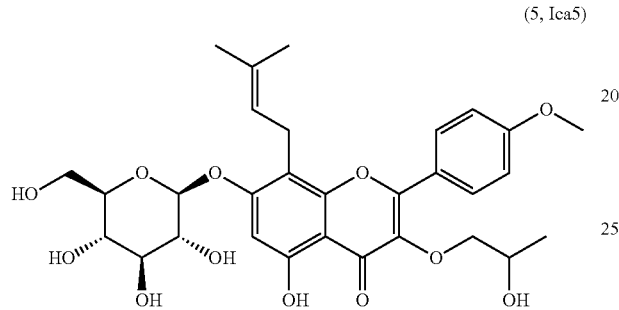

(5, Ica5)

Compound 5 (Ica5) was synthesized using a procedure similar to that used to prepare 3. A stirred suspension of 2 (150 mg), 1-bromo-2-propanol (0.2 mL), and anhydrous $K_2CO_3$ (230 mg) in dry acetone (35 mL) was refluxed at 75° C. for 6 hours. After the reaction mixture cooled, the solvent was evaporated under reduced pressure, and the residue was suspended in 200 mL $H_2O$ and extracted with EtOAc (3×200 mL). The organic layer was dried over anhydrous $Na_2SO_4$, and evaporated under reduced pressure. The residue was purified by column chromatography on LH20 (MeOH) to afford 5 (11.3 mg). $^1$H NMR (DMSO-$d_6$, 400 MHz), δ 8.13 (2H, d, J=8.8 Hz, H-2', 6'), 7.13 (2H, d, J=8.8 Hz, H-3', 5'), 6.61 (1H, s, H-6), 5.19 (1H, t, J=6.4 Hz, H-12), 4.41-5.35 (4H, m, Glu-OH), 5.00 (1H, d, J=6.8 Hz, Glu-H), 3.17-3.73 (6H, m, Glu-H), 4.84 (1H, m, H-17), 3.86 (2H, m, H-16), 3.86 (3H, s, $OCH_3$), 3.43 (2H, m, H-11), 1.74, 1.62 (3H, 3H, s, $CH_3$-14, 15). 1.08 (1H, d, J=6.4 Hz, H-18). ESIMS (positive-ion mode) m/z 589 [M+H]$^+$. purity: 97.22%, retention time=9.56 min.

Compound 5 was isolated using the procedure described above as a mixture of isomers at the 2-hydroxypropyl substituent. Isomer 5a of 5 can be depicted as follows:

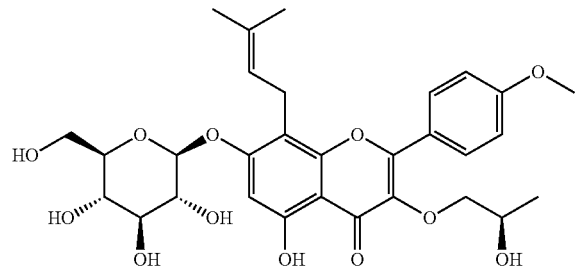

Isomer 5$^b$ of 5 can be depicted as follows:

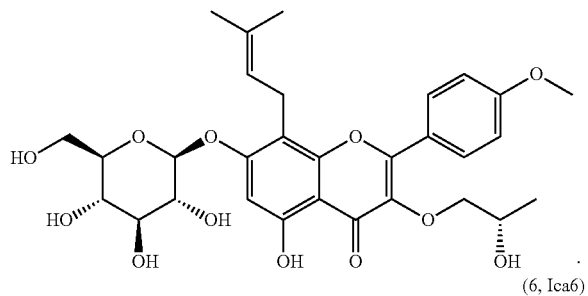

(6, Ica6)

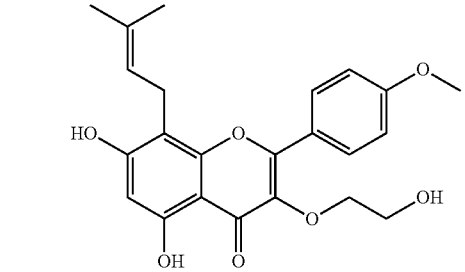

Compound 6 (Ica6) was synthesized using a procedure similar to that used to prepare 1. A solution of 3 (5 mg) in DMSO (1 mL) was added to a 0.1 M Na acetate buffer (pH 5.7, 50 mL) at 37° C. containing cellulase (10 mg). The suspension obtained was stirred at 37° C. overnight. Then, the mixture was extracted with EtOAc (3×10 mL). The organic layer was dried over anhydrous $Na_2SO_4$ and evaporated under reduced pressure. The residue was purified by column chromatography on LH20 (MeOH) to afford 6 (1.8 mg). $^1$H NMR (DMSO-$d_6$, 400 MHz), δ 12.56 (1H, s, OH-5), 8.13 (2H, d, J=8.8 Hz, H-2', 6'), 7.10 (2H, d, J=9.2 Hz, H-3', 5'), 6.23 (1H, s, H-6), 5.17 (1H, t, J=6.8 Hz, H-12), 4.03 (2H, t, J=4.8 Hz, H-16), 3.64 (2H, t, J=4.8 Hz, H-17), 3.85 (3H, s, $OCH_3$), 3.43 (2H, m, H-11), 1.73, 1.62 (3H, 3H, s, $CH_3$-14, 15). ESIMS (positive-ion mode) m/z 413 [M+H]$^+$. 95.08%, retention time=12.27 min.

(7, Ica7)

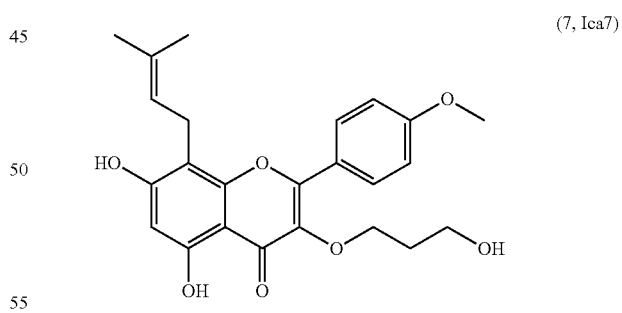

Compound 7 (Ica7) was synthesized using a procedure similar to that used to prepare 6. A solution of 4 (5 mg) in DMSO (1 mL) was added to a 0.1 M Na acetate buffer (pH 5.7, 50 mL) at 37° C. containing cellulase (10 mg). The suspension obtained was stirred at 37° C. overnight. Then, the mixture was extracted with EtOAc (3×10 mL). The organic layer was dried over anhydrous $Na_2SO_4$ and evaporated under reduced pressure. The residue was purified by column chromatography on LH20 (MeOH) to afford 7 (1.0 mg). $^1$H NMR (DMSO-$d_6$, 400 MHz), δ 12.57 (1H, s, OH-5), 8.01 (2H, d, J=8.8 Hz, H-2', 6'), 7.12 (2H, d, J=8.8

Hz, H-3', 5'), 6.13 (1H, s, H-6), 5.17 (1H, t, J=6.4 Hz, H-12), 4.02 (1H, t, J=6.8 Hz, H-18), 3.47 (1H, t, J=6.4 Hz, H-16), 3.85 (3H, s, OCH$_3$), 3.34 (2H, d, J=6.4 Hz, H-11), 1.77 (1H, t, J=6.4 Hz, H-17), 1.72, 1.62 (3H, 3H, s, CH$_3$-14, 15). ESIMS (positive-ion mode) m/z 427 [M+H]$^+$. 99.62%, retention time=12.71 min.

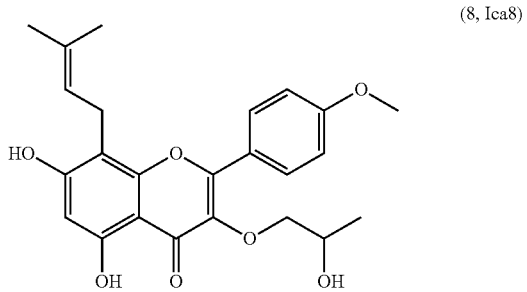 [SMILES: COc1ccc(-c2oc3c(CC=C(C)C)c(O)cc(O)c3c(=O)c2OCC(C)O)cc1]

(8, Ica8)

Compound 8 (Ica8) was synthesized using a procedure similar to that used to prepare 6. A solution of 5 (5 mg) in DMSO (1 mL) was added to a 0.1 M Na acetate buffer (pH 5.7, 50 mL) at 37° C. containing cellulase (10 mg). The suspension obtained was stirred at 37° C. overnight. Then, the mixture was extracted with EtOAc (3×10 mL). The organic layer was dried over anhydrous Na$_2$SO$_4$ and evaporated under reduced pressure. The residue was purified by column chromatography on LH20 (MeOH) to afford 8 (2.4 mg). $^1$H NMR (DMSO-d$_6$, 400 MHz), δ 12.49 (1H, s, OH-5), 8.04 (2H, d, J=8.8 Hz, H-2', 6'), 7.08 (2H, d, J=8.8 Hz, H-3', 5'), 5.76 (1H, s, H-6), 5.15 (1H, m, H-12), 3.74 (1H, m, H-17), 3.87 (2H, m, H-17), 3.84 (3H, s, OCH$_3$), 3.28 (2H, m, H-11), 1.71, 1.61 (3H, 3H, s, CH$_3$-14, 15). 1.04 (1H, d, J=6.4 Hz, H-18). ESIMS (positive-ion mode) m/z 427 [M+H]$^+$. 98.26%, retention time=13.11 min.

Compound 8 was isolated using the procedure described above as a mixture of isomers at the 2-hydroxypropyl substituent. Isomer 8$^a$ of 8 can be depicted as follows:

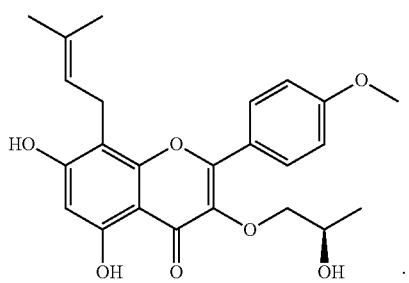

Isomer 8$^b$ of 8 can be depicted as follows:

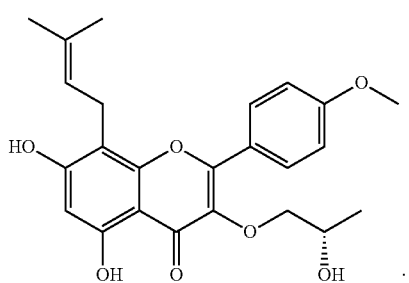 [SMILES: COc1ccc(-c2oc3c(CC=C(C)C)c(O)cc(O)c3c(=O)c2OC[C@H](C)O)cc1]

Compound 9 (Ica9) was synthesized using a procedure similar to that used to prepare 6. A solution of 2 (10 mg) in DMSO (1 mL) was added to a 0.1 M Na acetate buffer (pH 5.7, 50 mL) at 37° C. containing cellulase (10 mg). The suspension obtained was stirred at 37° C. overnight. Then, the mixture was extracted with EtOAc (3×10 mL). The organic layer was dried over anhydrous Na$_2$SO$_4$ and evaporated under reduced pressure. The residue was purified by column chromatography on LH20 (MeOH) to afford 9 (6.7 mg). $^1$H NMR (DMSO-d$_6$, 400 MHz), δ 12.36 (1H, s, OH-5), 8.12 (2H, d, J=8.8 Hz, H-2', 6'), 7.12 (2H, d, J=8.8 Hz, H-3', 5'), 6.29 (1H, s, H-6), 5.18 (1H, t, J=6.8 Hz, H-12), 3.85 (3H, s, OCH$_3$), 3.43 (2H, d, J=6.8 Hz, H-11), 1.75, 1.63 (3H, 3H, s, CH$_3$-14, 15). ESIMS (positive-ion mode) m/z 369 [M+H]$^+$. 97.88%, retention time=13.68 min.

In vitro PDE5 Inhibition Assay. cGMP (purchased from Enzo Life Sciences, Product No. BML-KI190-0002) at a concentration 1/10 of the K$_m$ of PDE5 was added to reaction buffer containing 40 mM tris hydrochloric acid and 10 mM magnesium chloride at pH 7.8. PDE5 (purified recombinant human PDE5 purchased from Abcam, Product No. AB125581) was added to start the reaction. The reaction was at room temperature until approximately 10-15% of cGMP in uninhibited control reactions was consumed. Keeping cGMP concentration low and staying within a linear reaction ensured that the reaction remained within Michaelis-Menten model assumptions and that the IC$_{50}$ could be approximated to the inhibition constant or K$_i$ (as substrate concentration decreases, IC$_{50}$ value approaches K$_i$ value). The reaction was stopped with the addition of 0.1 M hydrochloric acid. The amount of GMP produced was measured by LC-MS.

Ligand Docking. The crystal structure of PDE5A1 in complex with icariside II (PDB ID: 2H44), removed of all non-protein atoms, was used as the starting model for ligand docking. Structures of icariin derivatives were generated by modifying the icarisiide II model from the crystal structure (PDB ligand: 7CA) in Avogadro, an open-source molecular builder and visualization tool, Version 1.2.0 (www.avogadro.cc), or MarvinSketch Version 17.18.0 (ChemAxon, Cambridge, Mass., USA). To constrain search space to the PDE5 binding site, Coot Version 0.8.8 was used to align icariin analog structures with icarisiide II in the 2H44 PDB structure and to save the new ligand coordinates. The protein and ligand were then input into ROSIE, the Rosetta Online Server, with parameters set to use the starting coordinates in the ligand file and generate ligand conformers with the BCL. All other parameters were set to their default settings. Solutions were evaluated manually from the top set of results based on the ability to recapitulate a similar binding orientation as icariside II in the PDE5A1 crystal structure as well as the ability to engage in substantial protein-ligand interactions.

REFERENCES (1) Bradshaw, R. A.; Dennis, E. A. *Handbook of Cell Signaling*; Academic Press, 2009.
(2) Friebe, A.; Sandner, P.; Schmidtko, A. Meeting Report of the 8th International Conference on cGMP "cGMP: Generators, Effectors, and Therapeutic Implications" at Bamberg, Germany, from Jun. 23 to 25, 2017. *Naunyn. Schmiedebergs. Arch. Pharmacol.* 2017, 390 (12), 1177-1188.
(3) Surapisitchat, J.; Beavo, J. A. Phosphodiesterase Families. In *Handbook of Cell Signaling*; Bradshaw, R. A., Dennis, E. A., Eds.; Elsevier/Academic Press: Amsterdam; Boston, 2010; pp 1409-1416.

(4) Francis, S. H.; Corbin, J. D. Phosphodiesterase-5. In *Handbook of Cell Signaling*; Bradshaw, R. A., Dennis, E. A., Eds.; Elsevier/Academic Press: Amsterdam; Boston, 2010; pp 1439-1444.
(5) Mehrotra, N.; Gupta, M.; Kovar, A.; Meibohm, B. The Role of Pharmacokinetics and Pharmacodynamics in Phosphodiesterase-5 Inhibitor Therapy. *Int. J. Impot. Res.* 2007, 19 (3), 253-264.
(6) Mostafa, T. Non-Sexual Implications of Phosphodiesterase Type 5 Inhibitors. *Sexual Medicine Reviews* 2017, 5 (2), 170-199.
(7) Li, F.-S.; Weng, J.-K. Demystifying Traditional Herbal Medicine with Modern Approach. *Nature Plants* 2017, 3 (8), 17109.
(8) Ma, H.; He, X.; Yang, Y.; Li, M.; Hao, D.; Jia, Z. The Genus Epimedium: An Ethnopharmacological and Phytochemical Review. *J. Ethnopharmacol.* 2011, 134 (3), 519-541.
(9) Xin, Z. C.; Kim, E. K.; Lin, C. S.; Liu, W. J.; Tian, L.; Yuan, Y. M.; Fu, J. Effects of Icariin on cGMP-Specific PDE5 and cAMP-Specific PDE4 Activities. *Asian J. Androl.* 2003, 5 (1), 15-18.
(10) Ning, H.; Xin, Z.-C.; Lin, G.; Banie, L.; Lue, T. F.; Lin, C.-S. Effects of Icariin on Phosphodiesterase-5 Activity in Vitro and Cyclic Guanosine Monophosphate Level in Cavernous Smooth Muscle Cells. *Urology* 2006, 68 (6), 1350-1354.
(11) Dell'Agli, M.; Galli, G. V.; Dal Cero, E.; Belluti, F.; Matera, R.; Zironi, E.; Pagliuca, G.; Bosisio, E. Potent Inhibition of Human Phosphodiesterase-5 by Icariin Derivatives. *J. Nat. Prod.* 2008, 71 (9), 1513-1517.
(12) Xin, Z.; Euikyung, K.; Tian, Z.; Lin, G.; Guo, Y. Icariin on Relaxation Effect of Corpus Cavernosum Smooth Muscle. *Chin. Sci. Bull.* 2001, 46 (14), 1186-1190.
(13) Zhang, K. Y. J.; Card, G. L.; Suzuki, Y.; Artis, D. R.; Fong, D.; Gillette, S.; Hsieh, D.; Neiman, J.; West, B. L.; Zhang, C.; et al. A Glutamine Switch Mechanism for Nucleotide Selectivity by Phosphodiesterases. *Mol. Cell* 2004, 15 (2), 279-286.
(14) Wang, H.; Liu, Y.; Huai, Q.; Cai, J.; Zoraghi, R.; Francis, S. H.; Corbin, J. D.; Robinson, H.; Xin, Z.; Lin, G.; et al. Multiple Conformations of Phosphodiesterase-5: Implications for Enzyme Function and Drug Development. *J. Biol. Chem.* 2006, 281 (30), 21469-21479.
(15) Ke, H.; Wang, H. Crystal Structures of Phosphodiesterases and Implications on Substrate Specificity and Inhibitor Selectivity. *Curr. Top. Med. Chem.* 2007, 7 (4), 391-403.
(16) Huai, Q.; Liu, Y.; Francis, S. H.; Corbin, J. D.; Ke, H. Crystal Structures of Phosphodiesterases 4 and 5 in Complex with Inhibitor 3-Isobutyl-1-Methylxanthine Suggest a Conformation Determinant of Inhibitor Selectivity. *J. Biol. Chem.* 2004, 279 (13), 13095-13101.
(17) Wang, H.; Ye, M.; Robinson, H.; Francis, S. H.; Ke, H. Conformational Variations of Both Phosphodiesterase-5 and Inhibitors Provide the Structural Basis for the Physiological Effects of Vardenafil and Sildenafil. *Mol. Pharmacol.* 2008, 73, 104-110.
(18) Shang, N.-N.; Shao, Y.-X.; Cai, Y.-H.; Guan, M.; Huang, M.; Cui, W.; He, L.; Yu, Y.-J.; Huang, L.; Li, Z.; et al. Discovery of 3-(4-Hydroxybenzyl)-1-(thiophen-2-Yl) Chromeno [2, 3-C] Pyrrol-9 (2H)-One as a Phosphodiesterase-5 Inhibitor and Its Complex Crystal Structure. *Biochem. Pharmacol.* 2014, 89 (1), 86-98.
(19) Schluesener, J. K.; Schluesener, H. Plant Polyphenols in the Treatment of Age-Associated Diseases: Revealing the Pleiotropic Effects of Icariin by Network Analysis. *Mol. Nutr. Food Res.* 2014, 58 (1), 49-60.
(20) Liu, D. F.; Li, Y. P.; Ou, T. M.; Huang, S. L.; Gu, L. Q.; Huang, M.; Huang, Z. S. Synthesis and Antimultidrug Resistance Evaluation of Icariin and Its Derivatives. *Bioorg. Med. Chem. Lett.* 2009, 19 (15), 4237-4240.
(21) Ming, L. G.; Chen, K. M.; Xian, C. J. Functions and Action Mechanisms of Flavonoids Genistein and Icariin in Regulating Bone Remodeling. *J. Cell. Physiol.* 2013, 228 (3), 513-521.
(22) Kim, D. H.; Jung, H. A.; Sohn, H. S.; Kim, J. W.; Choi, J. S. Potential of Icariin Metabolites from Epimedium Koreanum Nakai as Antidiabetic Therapeutic Agents. *Molecules* 2017, 22 (6).
(23) Chen, G.; Wang, H.; Robinson, H.; Cai, J.; Wan, Y.; Ke, H. An Insight into the Pharmacophores of Phosphodiesterase-5 Inhibitors from Synthetic and Crystal Structural Studies. *Biochem. Pharmacol.* 2008, 75 (9), 1717-1728.
(24) Jingshan Shen, Shujun Zhang, Hongli Guo, Xinjian Chen, Yifeng Nian. Prenyl Flavonoids, their Preparation and Use. 2008014722A1.
(25) Hanwell, M. D.; Curtis, D. E.; Lonie, D. C.; Vandermeersch, T.; Zurek, E.; Hutchison, G. R. Avogadro: An Advanced Semantic Chemical Editor, Visualization, and Analysis Platform. *J. Cheminform.* 2012, 4 (1), 17.
(26) Emsley, P.; Cowtan, K. Coot: Model-Building Tools for Molecular Graphics. *Acta Crystallogr. D Biol. Crystallogr.* 2004, 60 (Pt 12 Pt 1), 2126-2132.
(27) Emsley, P.; Lohkamp, B.; Scott, W. G.; Cowtan, K. Features and Development of Coot. *Acta Crystallogr. D Biol. Crystallogr.* 2010, 66 (Pt 4), 486-501.
(28) Lyskov, S.; Chou, F.-C.; Conchúir, S. Ó.; Der, B. S.; Drew, K.; Kuroda, D.; Xu, J.; Weitzner, B. D.; Renfrew, P. D.; Sripakdeevong, P.; et al. Serverification of Molecular Modeling Applications: The Rosetta Online Server That Includes Everyone (ROSIE). *PLoS One* 2013, 8 (5), e63906.

The relevant teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A compound represented by the following structural formula:

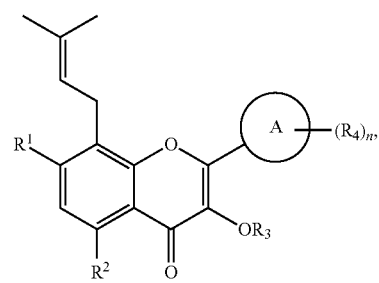

or a pharmaceutically acceptable salt thereof, wherein:
$R^1$ is —O-monosaccharide, hydroxy, hydrogen, halogen or carboxy, or —C(O)O($C_1$-$C_{10}$)alkyl, —C(O)O($C_1$-$C_{10}$)alkenyl or —C(O)O($C_1$-$C_{10}$)alkynyl optionally substituted with one or more substituents independently selected from $(C_1-C_5)$alkylamino, $(C_1-C_5)$alkoxy, amino, cyano, $(C_1-C_5)$dialkylamino, halo$(C_1-C_5)$alkoxy, halogen, hydroxy, nitro, thio or thio$(C_1-C_5)$alkoxy;

$R^2$ is hydroxy, —O-monosaccharide, hydrogen, halogen or $(C_1-C_{10})$alkoxy optionally substituted with one or more substituents independently selected from $(C_1-C_5)$alkylamino, $(C_1-C_5)$alkoxy, amino, cyano, $(C_1-C_5)$dialkylamino, halo$(C_1-C_5)$alkoxy, halogen, hydroxy, nitro, thio or thio$(C_1-C_5)$alkoxy;

$R^3$ is hydroxy$(C_1-C_5)$alkyl;

Ring A is a $(C_3-C_{15})$unsaturated or aromatic carbocyclyl or a $(C_3-C_{15})$unsaturated or aromatic heterocyclyl;

each $R^4$ is independently $(C_1-C_{10})$alkyl, $(C_1-C_{10})$alkylamino, $(C_1-C_{10})$alkenyl, $(C_1-C_{10})$alkenoxy, $(C_1-C_{10})$alkoxy, $(C_1-C_{10})$alkynyl, $(C_1-C_{10})$acyl, $(C_1-C_{10})$alkanoyl, amido, amino, formyl, $(C_6-C_{15})$aryl, $(C_6-C_{15})$aryloxy, carboxy, cyano, $(C_3-C_{15})$cycloalkyl, $(C_3-C_{15})$cycloalkoxy, $(C_1-C_{10})$dialkylamino, $(C_1-C_{10})$ether, halo$(C_1-C_{10})$alkyl, halo$(C_1-C_{10})$alkoxy, halogen, $(C_5-C_{13})$heteroaryl, $(C_5-C_{15})$heteroaryloxy, $(C_3-C_{15})$heterocyclyl, $(C_3-C_{15})$heterocyclyloxy, hydroxy, nitro, phosphate, phosphonate, sulfate, sulfonyl, sulfonamide, sulfonate, thio or thio$(C_1-C_{10})$alkoxy; and n is 0, 1, 2, 3, 4, 5, 6, 7, 8, 9, 10, 11, 12, 13 or 14.

2. The compound of claim 1, wherein $R^1$ is —O-monosaccharide or hydroxy.

3. The compound of claim 2, wherein $R^1$ is —O-monosaccharide.

4. The compound of claim 3, wherein $R^1$ is a hexose.

5. The compound of claim 4, wherein $R^1$ is selected from allose, altrose, glucose, mannose, gulose, idose, galactose, talose, psicose, fructose, sorbose, tagatose, fucose or rhamnose.

6. The compound of claim 5, wherein $R^1$ is glucose.

7. The compound of claim 2, wherein $R^1$ is hydroxy.

8. The compound of claim 1, wherein $R^2$ is hydroxy.

9. The compound of claim 1, wherein $R^3$ is hydroxyethyl or hydroxypropyl.

10. The compound of claim 1, wherein $R^3$ is 2-hydroxyethyl, 3-hydroxypropyl or 2-hydroxypropyl.

11. The compound of claim 1, wherein Ring A is a $(C_6-C_{15})$aryl or a $(C_5-C_{15})$heteroaryl.

12. The compound of claim 11, wherein Ring A is a $C_5$ heteroaryl and n is 0, 1, 2, 3 or 4; or Ring A is a $C_6$ heteroaryl and n is 0, 1, 2, 3, 4 or 5.

13. The compound of claim 1, represented by the following structural formula:

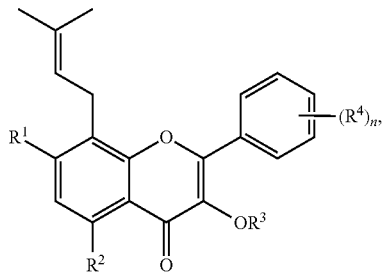

or a pharmaceutically acceptable salt thereof, wherein n is 0, 1, 2, 3, 4 or 5.

14. The compound of claim 13, represented by the following structural formula:

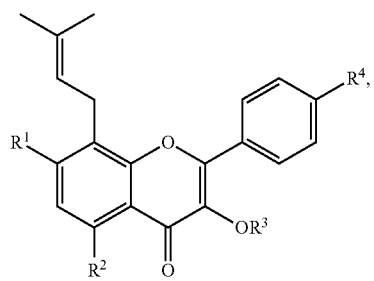

or a pharmaceutically acceptable salt thereof.

15. The compound of claim 1, wherein n is 1.

16. The compound of claim 1, wherein each monosaccharide is independently selected from a pentose and a hexose.

17. The compound of claim 16, wherein each pentose is independently selected from arabinose, lyxose, ribose, xylose, ribulose, xylulose, deoxyribose or fuculose.

18. The compound of claim 16, wherein each hexose is independently selected from allose, altrose, glucose, mannose, gulose, idose, galactose, talose, psicose, fructose, sorbose, tagatose, fucose or rhamnose.

19. A compound represented by the following structural formula:

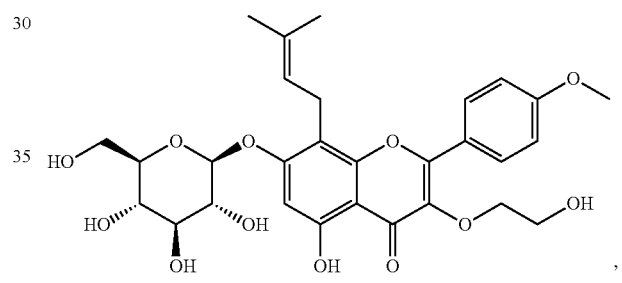

or a pharmaceutically acceptable salt thereof.

20. A compound represented by the following structural formula:

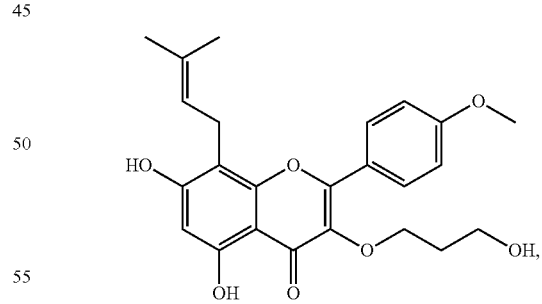

or a pharmaceutically acceptable salt thereof.

21. A composition comprising a compound of claim 1, or a pharmaceutically acceptable salt thereof, and a pharmaceutically acceptable carrier or excipient.

22. A method of treating a cardiovascular, gastrointestinal, pulmonary, musculoskeletal, neurological or reproductive disease, disorder or condition in a subject in need thereof, comprising administering to the subject an effective amount of a compound of claim 1, or a pharmaceutically acceptable salt thereof.

23. A method of treating a cancer in a subject in need thereof, comprising administering to the subject an effective amount of a compound of claim 1, or a pharmaceutically acceptable salt thereof.

24. A method of treating an inflammatory or autoimmune disease, disorder or condition in a subject in need thereof, comprising administering to the subject an effective amount of a compound of claim 1, or a pharmaceutically acceptable salt thereof.

* * * * *